(12) United States Patent
Hallam et al.

(10) Patent No.: US 9,795,591 B2
(45) Date of Patent: Oct. 24, 2017

(54) PHOSPHODIESTERASE 4 INHIBITORS FOR COGNITIVE AND MOTOR REHABILITATION

(75) Inventors: Thomas M. Hallam, Astoria, NY (US); Tim Tully, Cold Spring Harbor, NY (US); Rusiko Bourtchouladze, New York, NY (US)

(73) Assignee: Dart Neuroscience (Cayman) Ltd., Grand Cayman (KY)

( * ) Notice: Subject to any disclaimer, the term of this patent is extended or adjusted under 35 U.S.C. 154(b) by 871 days.

(21) Appl. No.: 13/439,022

(22) Filed: Apr. 4, 2012

(65) Prior Publication Data

US 2012/0196898 A1  Aug. 2, 2012
US 2017/0224845 A9  Aug. 10, 2017

Related U.S. Application Data

(60) Continuation of application No. 11/750,900, filed on May 18, 2007, now Pat. No. 8,153,646, and a continuation-in-part of application No. 11/479,185, filed on Jun. 29, 2006, now Pat. No. 8,097,647, which is a division of application No. 10/410,508, filed on Apr. 8, 2003, now abandoned, which is a continuation-in-part of application No. 09/927,914, filed on Aug. 10, 2001, now Pat. No. 7,947,731, and a continuation of application No. 12/041,188, filed on Mar. 3, 2008, which is a continuation of application No. PCT/US2007/069279, filed on May 18, 2007.

(60) Provisional application No. 60/801,949, filed on May 19, 2006.

(51) Int. Cl.

| A61K 31/435 | (2006.01) |
| A61K 31/445 | (2006.01) |
| A61K 31/45 | (2006.01) |
| A61K 31/40 | (2006.01) |
| A61K 31/00 | (2006.01) |
| A61K 31/4418 | (2006.01) |
| A61K 48/00 | (2006.01) |

(52) U.S. Cl.
CPC .............. *A61K 31/40* (2013.01); *A61K 31/00* (2013.01); *A61K 31/435* (2013.01); *A61K 31/445* (2013.01); *A61K 31/4418* (2013.01); *A61K 31/45* (2013.01); *A61K 48/00* (2013.01)

(58) Field of Classification Search
CPC ...... A61K 31/10; A61K 31/165; A61K 31/40; A61K 31/4015; A61K 31/435; A61K 31/445; A61K 31/45
See application file for complete search history.

(56) References Cited

U.S. PATENT DOCUMENTS

| 4,394,385 | A |   | 7/1983 | Cragoe, Jr. | |
| 5,059,612 | A |   | 10/1991 | Imanishi et al. | |
| 5,434,149 | A | * | 7/1995 | Jonas et al. | 514/222.5 |
| 5,624,898 | A |   | 4/1997 | Frey | |
| 5,798,246 | A |   | 8/1998 | Au Young et al. | |
| 5,965,568 | A | * | 10/1999 | Kakihana et al. | 514/283 |
| 6,270,077 | B1 | * | 8/2001 | Cohen | 273/273 |
| 6,290,994 | B1 | * | 9/2001 | Flores et al. | 424/725 |

FOREIGN PATENT DOCUMENTS

| EP | 2377533 A2 | 10/2011 |
| WO | 9528926 | 11/1995 |
| WO | 0014083 | 3/2000 |
| WO | 0213867 A | 2/2002 |
| WO | 0245749 A | 6/2002 |
| WO | 03032981 A | 4/2003 |
| WO | 03065994 A | 8/2003 |
| WO | 2004/082624 | 9/2004 |
| WO | 2004091609 A | 10/2004 |
| WO | 2006110588 A | 10/2006 |

OTHER PUBLICATIONS

Pearse, D. D. et al, Nat. Med. 10(6): 610-6 (2004).
Nikulina, E. et al., Proc. Natl. Acad. Sci. U.S.A. 101(23) 8786-90 (2004).
Carter et al., American Journal of Occupational Therapy, 37(5) pp. 320-326 (1983).
Bourtchouladze et al., Proceedings of the National Academy of Sciences 100(18) pp. 10518-10522 (2003.
G. M. Rose et al., Current Pharmaceutical Design, 11(26) pp. 3329-3334 (2005).
Imanishi, T. et al., European Journal of Pharmacology Investigation, Amsterdam, NL, 321(3) pp. 273-278 (1997).
Gong, et al. The Journal of Clinical Investigation, 114(11) pp. 1624-1634 (2004).
Dean et al., Task-Related Training Improves Performance of Seated Reaching Tasks After Stroke, 1997, Stroke, vol. 28, pp. 722-728.
Grant et al., Therapeutic Nutraceutical Treatments for Osteoarthritis and Ischaemia, Jan. 2000, Exp. Ther. Patents, Exp. Ther. Patents, pp. 39-48.
Krebs et al., Quantization of Continous Arm Movements in Humans with Brain Injury, Apr. 1999, Neurobiology, vol. 96, pp. 4645-4649.
Nibuya et al., Chronic Antidepressant Administration Increases the Expression of cAMP Response Element Binding Protein (CREB) in Rat Hippocampus, Apr. 01, 1996, the Journal of Neuroscience, vol. 16, issue 1, pp. 2365-2372.
Rao et al., Effects of Acute and Repeated Dose Administration of Caffeine and Pentoxifylline on Diazepam-Induced Mouse Behavior in the Hole-Board Test, Psychopharmacology, 1999, vol. 144, pp. 61-66.
Ward, Pentoxifylline, Jul. 1987, Drugs, vol. 34, issue 1, pp. 50-97.

\* cited by examiner

*Primary Examiner* — Yong Chong
(74) *Attorney, Agent, or Firm* — McCarter & English, LLP

(57) ABSTRACT

The present invention provides methods of improving cognitive and motor deficits associated with central nervous system (CNS) disorder or condition in an animal. The methods comprise a general administration of phosphodiesterase 4 inhibitors and optionally training the animal under conditions sufficient to produce an improvement in performance.

8 Claims, 7 Drawing Sheets

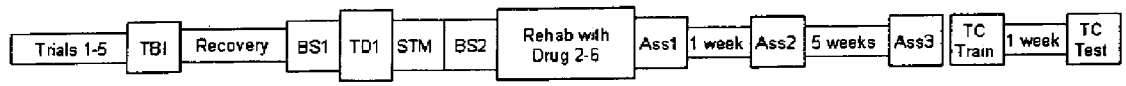
FIG. 1 Time course of Object Recognition Trials: Trial consisted of a single training session followed by a testing session 24 hrs later (except the 4hr interval for the STM trial).

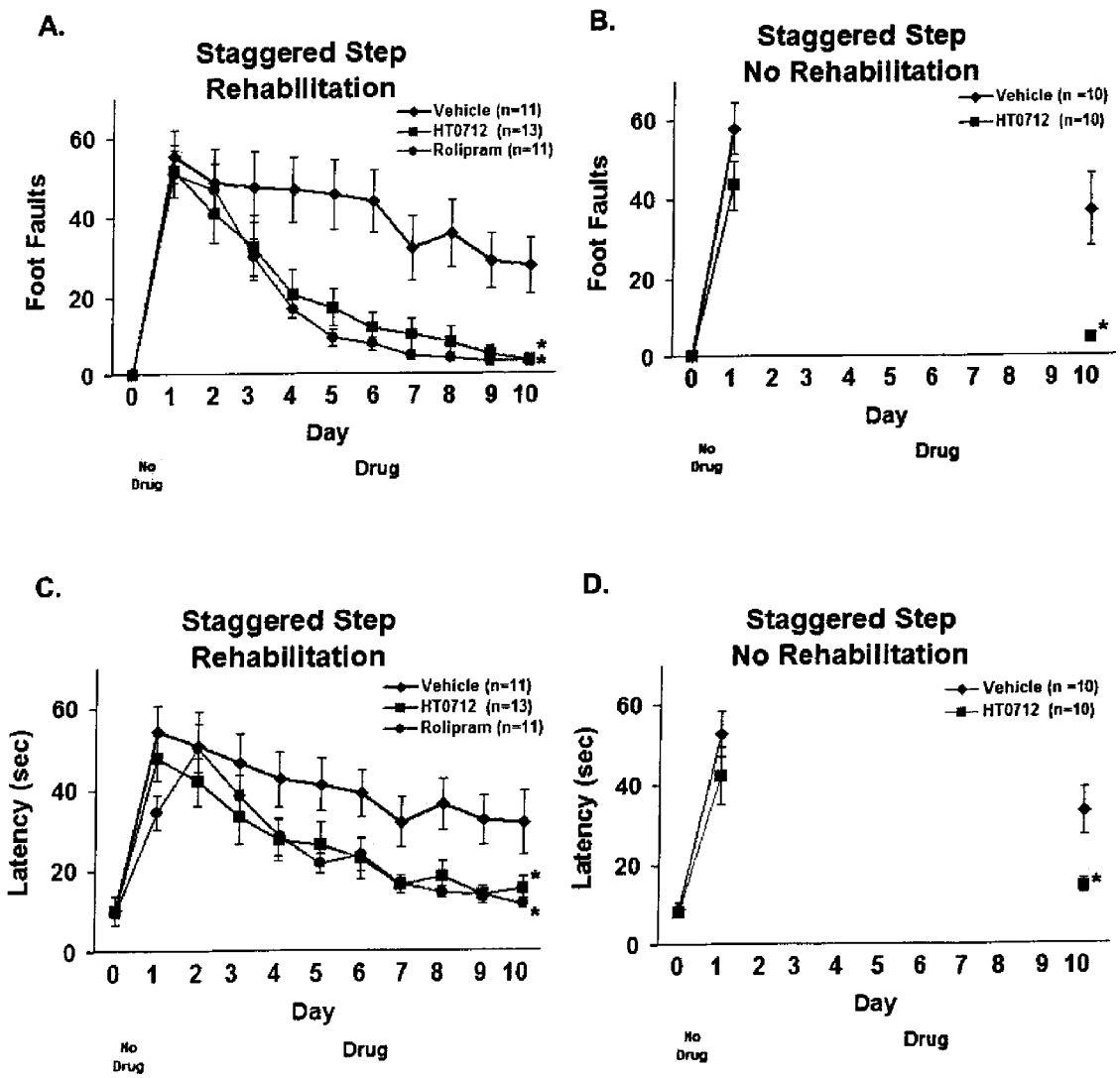
FIG. 2 – Locomotor Rehabilitation on the Staggered Step

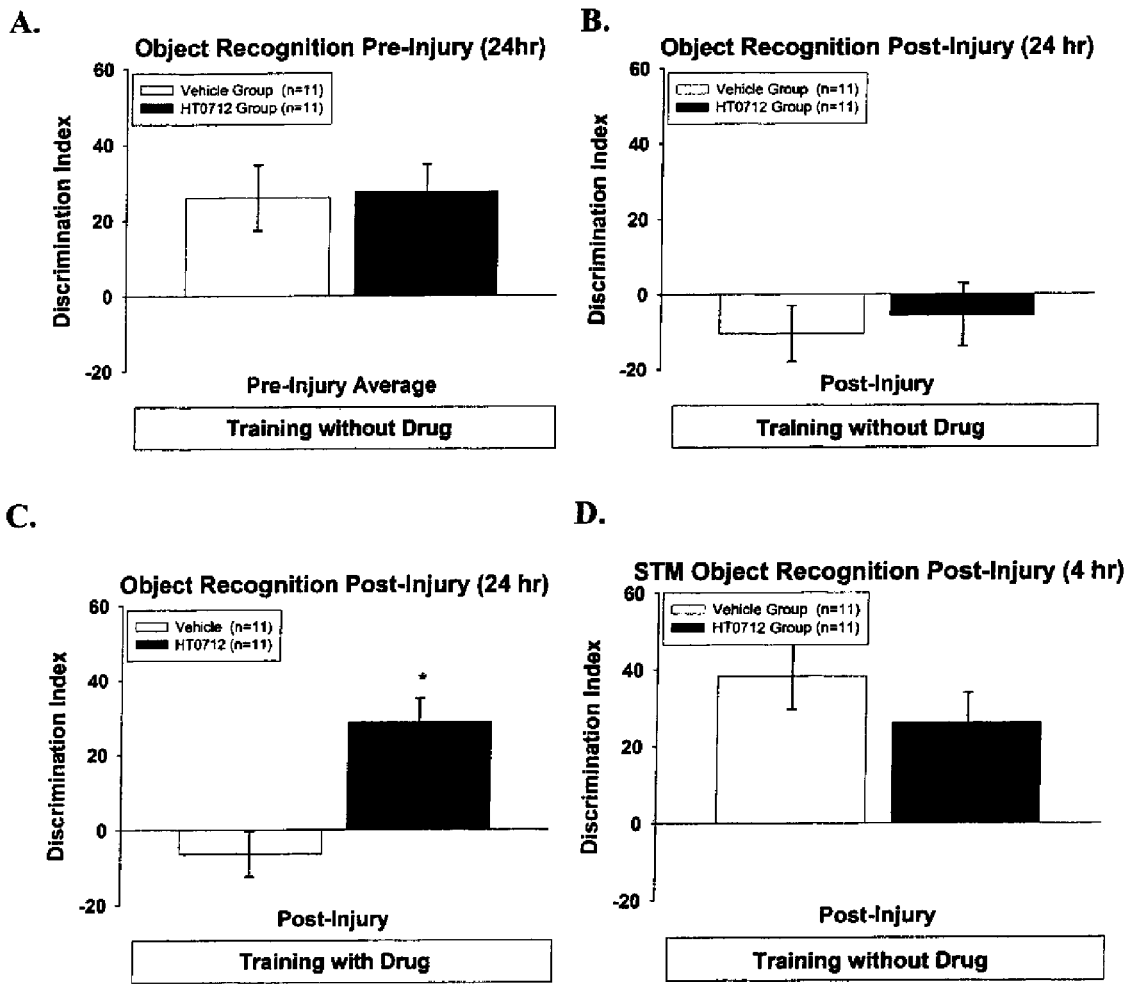
FIG. 3A, 3B, 3C and 3D Object recognition performance (mean DI ± S.E.M.).

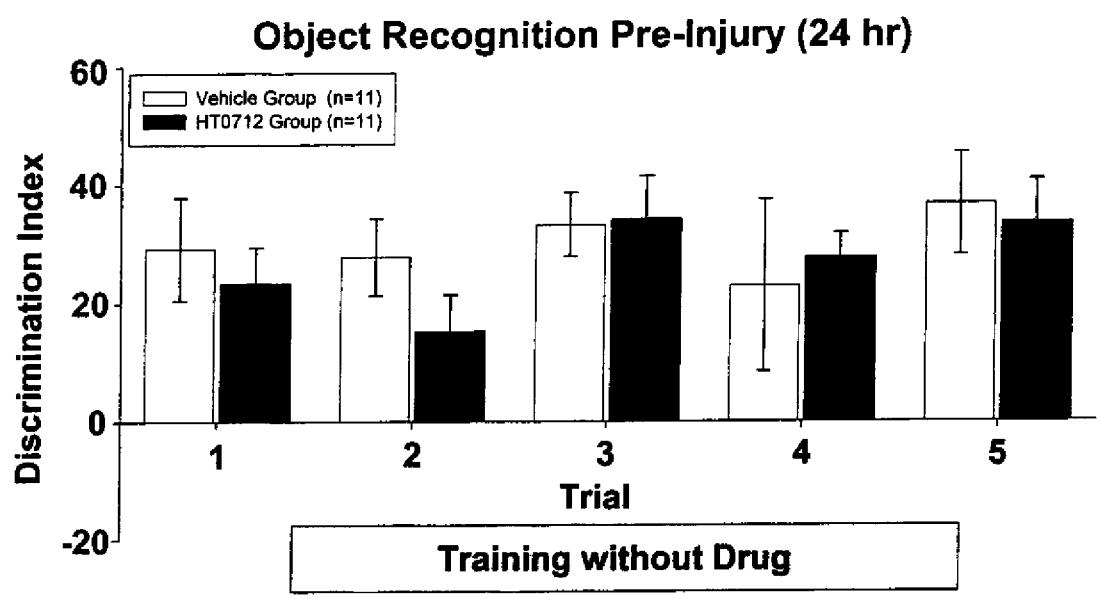
FIG. 3E: Object recognition performance in rats prior to injury

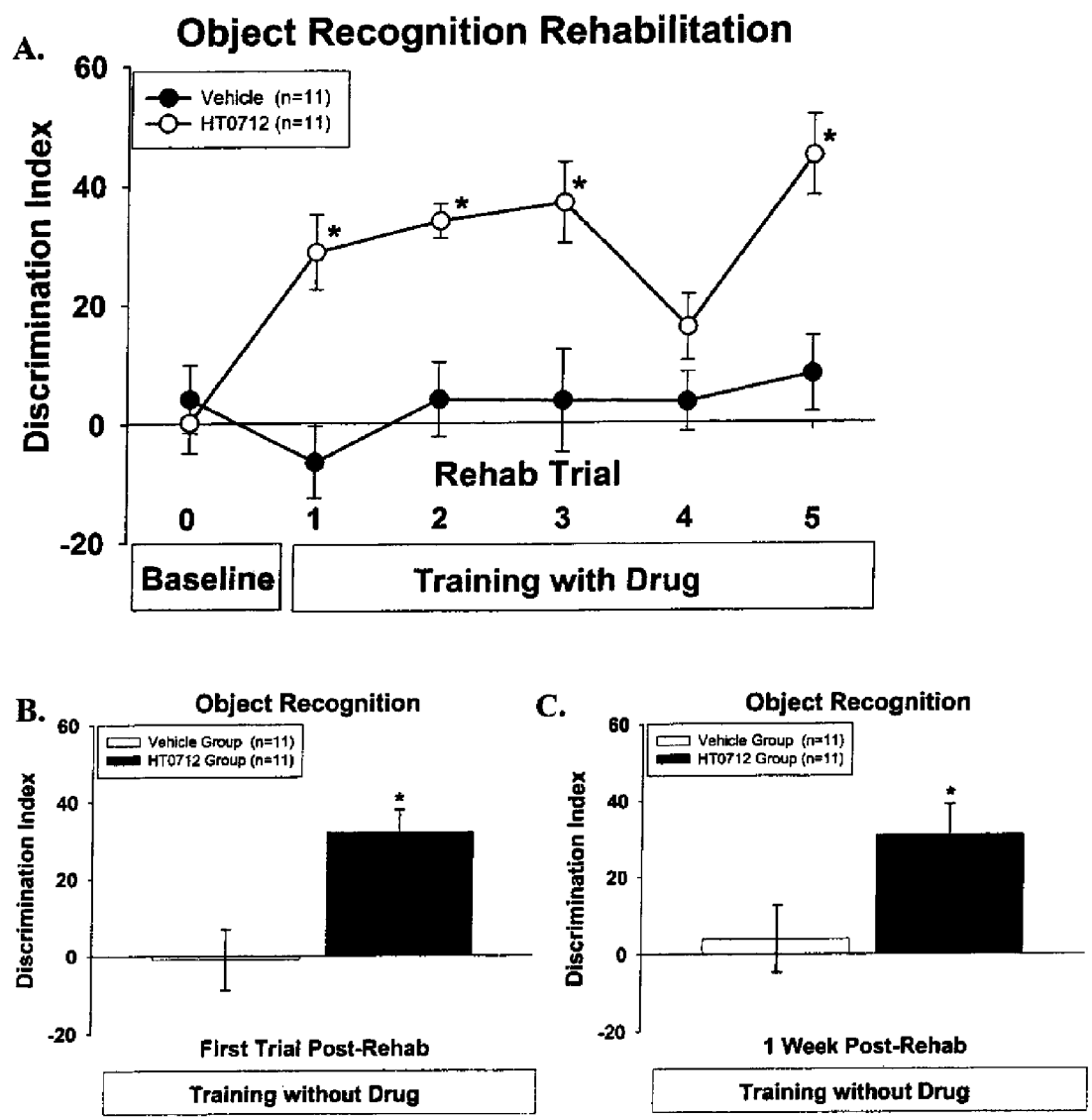
FIG. 4A, 4B and 4C: Drug assisted cognitive rehabilitation performance (mean DI ± SEM).

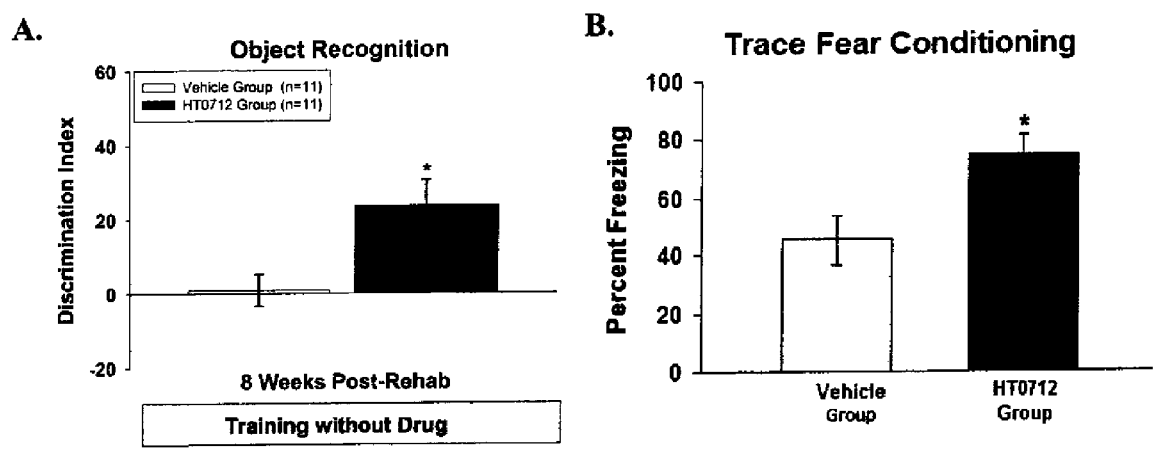
FIG. 5A and 5B: Long lasting effects of cognitive rehabilitation

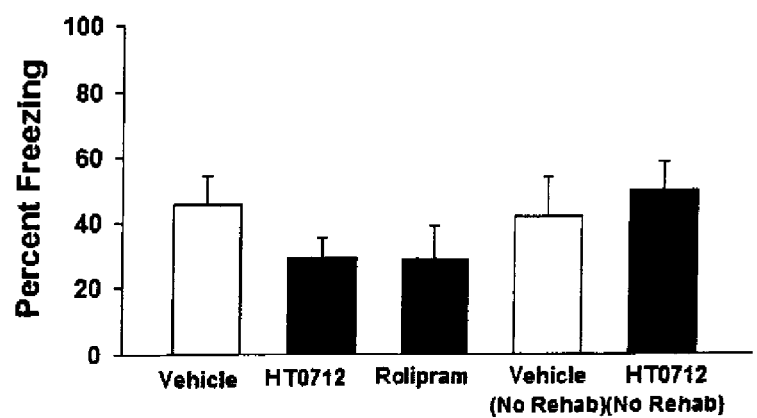
FIG. 5C: Memory performance for trace fear conditioning in motor-rehabilitation animals.

PHOSPHODIESTERASE 4 INHIBITORS FOR COGNITIVE AND MOTOR REHABILITATION

CROSS-REFERENCE TO RELATED APPLICATIONS

This application, filed pursuant to 37 C.F.R. §1.53(b), is a continuation of U.S. application Ser. No. 11/750,900, filed May 18, 2007, now U.S. Pat. No. 8,153,646, which is a continuation-in-part of U.S. application Ser. No. 11/479,185, filed Jun. 29, 2006, now U.S. Pat. No. 8,097,647, which is a divsional of U.S. application Ser. No. 10/410,508, filed Apr. 8, 2003, now abandoned. This application is also a continuation of U.S. application Ser. No. 12/041,188, filed Mar. 3, 2008, which is a divisional of U.S. application Ser. No. 11/750,900, filed May 18, 2007, now U.S. Pat. No. 8,153,646, which is a continuation-in-part of U.S. application Ser. No. 11/479,185, filed Jun. 29, 2006, now U.S. Pat. No. 8,097,647, which is a divisional of U.S. application Ser. No. 10/410,508, filed Apr. 8, 2003, now abandoned; U.S. application Ser. No. 12/041,188 is also a continuation of International Application No. PCT/US2007/069279, filed May 18, 2007, which claims the benefit of U.S. Provisional Application No. 60/801,949, filed May 19, 2006.

BACKGROUND OF THE INVENTION

An estimated 4 to 5 million Americans (about 2% of all ages and 15% of those older than age 65) have some form and degree of cognitive failure. Cognitive failure (dysfunction or loss of cognitive functions, the process by which knowledge is acquired, retained and used) commonly occurs in association with central nervous system (CNS) disorders or conditions, including age-associated memory impairment, delirium (sometimes called acute confusional state), dementia (sometimes classified as Alzheimer's or non-Alzheimer's type), Alzheimer's disease, Parkinson's disease, Huntington's disease (chorea), mental retardation, cerebrovascular disease (e.g., stroke, ischemia), affective disorders (e.g., depression), psychotic disorders (e.g., schizophrenia, autism (Kanner's Syndrome)), neurotic disorders (e.g., anxiety, obsessive-compulsive disorder), attention deficit disorder (ADD), subdural hematoma, normal-pressure hydrocephalus, brain tumor, head or brain trauma.

Cognitive dysfunction is typically manifested by one or more cognitive deficits, which include memory impairment (impaired ability to learn new information or to recall previously learned information), aphasia (language/speech disturbance), apraxia (impaired ability to carry out motor activities despite intact motor function), agnosia (failure to recognize or identify objects despite intact sensory function), disturbance in executive functioning (i.e., planning, organizing, sequencing, abstracting).

Cognitive dysfunction causes significant impairment of social and/or occupational functioning, which can interfere with the ability of an individual to perform activities of daily living and greatly impact the autonomy and quality of life of the individual.

Cognitive training protocols are generally employed in rehabilitating individuals who have some form and degree of cognitive dysfunction. For example, cognitive training protocols are commonly employed in stroke rehabilitation and in age-related memory loss rehabilitation. Because multiple training sessions are often required before an improvement or enhancement of a specific aspect of cognitive performance (ability or function) is obtained in the individuals, cognitive training protocols are often very costly and time-consuming.

Human brain injury often results in motor and cognitive impairments. While advances in critical care medicine and patient management have led to improvements in patient outcome following traumatic brain injury (TBI), there is currently no known treatment to prevent the neuronal cell death and dysfunction that follows TBI. Although multiple treatments have proven neuroprotective in pre-clinical models of TBI, most have failed to show efficacy in humans.

Once a patient is stabilized following TBI, the standard of care dictates extensive motor or cognitive rehabilitation. During this rehabilitation the patient often regains lost skills, finally resulting in improved functional outcome. It would be beneficial if pharmaceutical treatments could be developed to enhance motor or cognitive rehabilitation following TBI, and thus improve functional outcome In the rat, the well characterized lateral fluid percussion (LFP) brain injury results in extensive apoptotic and necrotic cell death in the hippocampus, thalamus, and cortex (including motor cortex). This neuronal death leads to neuronal dysfunction and impairments in multiple brain systems. Studies have documented deficits in motor and cognitive function (Hamm, R. J. et al., Behav. Brain Res., 59(1-2): 169-173 (1993); Gong et al., Brain Res., 700(1-2):299-302 (1995); Hamm, R. J., J. Neurotrauma., 18(11):1207-16 (2001); Floyd et al., J Neurotrauma., 19(3):303-16 (2002); Hallam et al., J Neurotrauma, 21(5):521-39 (2004)) following LFP brain injury. Extensive rehabilitation can result in improved neurobehavioral outcome following various experimental brain injuries. Current theories hold that during rehabilitation, neurons within the damaged brain tissue and surrounding the damaged area are re-trained to assume some of the lost function. This "re-training" is a form of learning and occurs through the induction of neural plasticity.

Numerous studies have shown that cyclic-AMP (cAMP) and the downstream transcription factor cAMP-responsive element binding protein (CREB) are key regulators in the induction of long-term memory and neural plasticity (Yin, J. C. et al., Cell, 79(1):49-58 (1994); Bourtchuladze, R. et al., Cell, 79(1):59-68 (1994); Impey, S. et al., Nat. Neurosci., 1(7):595-601 (1998)). Genetic or pharmacological interventions which impair cAMP/CREB signaling impair long-term memory formation and synaptic plasticity. Conversely, genetic or pharmacological interventions which enhance cAMP/CREB signaling facilitate long term memory formation and synaptic plasticity.

SUMMARY OF THE INVENTION

The present invention relates to administration of cyclic AMP response element binding protein (CREB) pathway-enhancing drugs to which can either (1) rehabilitate various forms of cognitive dysfunction more efficiently than any current method, (2) enhance normal cognitive performance (ability or function), (3) rehabilitate various forms of motor dysfunction more efficiently than any current method, or (4) enhance normal motor performance (ability or function). Administration of cyclic AMP response element binding protein (CREB) pathway-enhancing drugs can be applied for any aspect of brain function that shows a lasting performance gain after cognitive or motor training. Accordingly, administration of cyclic AMP response element binding protein (CREB) pathway-enhancing drugs can be used in rehabilitating an animal with some form and degree of cognitive or motor dysfunction or in enhancing (improving) normal cognitive or motor performance in an animal. Administration of cyclic AMP response element binding protein (CREB) pathway-enhancing drugs can also be used to fine-tune the synaptic connections of newly acquired, transplanted stem cells that differentiate into neurons.

As described herein, the administration of cyclic AMP response element binding protein (CREB) pathway-enhancing drugs can be done alone or in the setting of Augmented Cognitive Training (ACT). ACT comprises two parts: (1) a specific training protocol for each brain (cognitive or motor) function and (2) administration of cyclic AMP response element binding protein (CREB) pathway-enhancing drugs. This combination can augment cognitive training by reducing the duration of and/or number of training sessions required to yield a performance gain relative to that obtained with cognitive training alone or by requiring shorter or no rest intervals between training sessions to yield a performance gain. This combination can also augment cognitive training by reducing the duration and/or number of training sessions required for the induction in a specific neuronal circuit(s) of a pattern of neuronal activity or by reducing the duration and/or number of training sessions or underlying pattern of neuronal activity required to induce CREB-dependent long-term structural/function (i.e., long-lasting) change among synaptic connections of the neuronal circuit. In this manner, the administration of cyclic AMP response element binding protein (CREB) pathway-enhancing drugs can improve the efficiency of existing cognitive training protocols, thereby yielding significant economic benefit.

As a result of the present invention, methods of enhancing a specific aspect of cognitive performance in an animal (particularly a human or other mammal or vertebrate) in need thereof are provided herein comprising (a) administering to the animal an augmenting agent which enhances CREB pathway function; and, optionally (b) training the animal under conditions sufficient to produce an improvement in performance of a cognitive task of interest by the animal.

"Augmenting agents" are also referred to herein as "CREB pathway-enhancing drugs".

Methods are provided herein for improving a cognitive deficit associated with a central nervous system (CNS) disorder or condition in an animal comprising treating the animal with an augmenting agent which enhances CREB pathway function in the absence of formal cognitive training. Methods are also provided herein for providing sustained improvement in a cognitive deficit associated with a central nervous system (CNS) disorder or condition in an animal comprising administering to the animal an augmenting agent which enhances CREB pathway function; and detecting said sustained improvement. In one embodiment the method further comprises training the animal under conditions sufficient to produce an improvement in performance of a particular cognitive task by the animal. CNS disorders and conditions include age-associated memory impairment, neurodegenerative diseases (e.g., Alzheimer's disease, Parkinson's disease, Huntington's disease (chorea), other senile dementia), psychiatric diseases (e.g., depression, schizophrenia, autism, attention deficit disorder), trauma dependent loss of function (e.g., cerebrovascular diseases (e.g., stroke, ischemia), brain tumor, head or brain injury), genetic defects (e.g., Rubinstein-Taybi syndrome, down syndrome, Angelman syndrome, neurofibromatosis, Coffin-Lowry syndrome, Rett syndrome, myotonic dystrophy, fragile X syndrome (e.g., fragile X-1, fragile X-2), William's syndrome) and learning disabilities. It is contemplated that treatment with an augmenting agent which enhances CREB pathway function results in sustained, maintained or permanent improvement in performance of the cognitive task by the animal after administration of the augmenting agent is stopped or discontinued.

Methods are provided herein for improving a cognitive deficit associated with mental retardation in an animal in need of said treatment comprising treating the animal with an augmenting agent which enhances CREB pathway function (e.g., a phosphodiesterase 4 inhibitor) in the absence of formal cognitive training. Methods are also provided herein for providing sustained improvement in a cognitive deficit associated with mental retardation in an animal comprising administering to the animal an augmenting agent which enhances CREB pathway function (e.g., a phosphodiesterase 4 inhibitor) and detecting said sustained improvement. In one embodiment, the method further comprises training the animal under conditions sufficient to produce an improvement in performance by the animal of a cognitive task whose deficit is associated with mental retardation. Mental retardation impacts cognitive processing and cognitive functions, including learning and memory acquisition. Mental retardation may be caused by chromosomal or genetic factors, congenital infections, teratogens (drugs and other chemicals), malnutrition, radiation or unknown conditions affecting implantation and embryogenesis. Mental retardation syndromes include Rubinstein-Taybi syndrome, down syndrome, Angelman syndrome, neurofibromatosis, Coffin-Lowry syndrome, Rett syndrome, myotonic dystrophy, fragile X syndrome (e.g., fragile X-1, fragile X-2) and William's syndrome (Weeber, E. J. et al., Neuron, 33:845-848 (2002)).

Methods are provided herein for improving a cognitive deficit associated with a CNS disorder or condition in an animal having undergone neuronal stem cell or glial stem cell manipulation comprising treating the animal with an augmenting agent which enhances CREB pathway function in the absence of formal cognitive training. Methods are also provided herein for providing sustained improvement in a cognitive deficit associated with a CNS disorder or condition in an animal having undergone neuronal stem cell manipulation comprising administering to the animal an augmenting agent which enhances CREB pathway function; and, detecting said sustained improvement. In one embodiment, the method further comprises training the animal under conditions sufficient to stimulate or induce neuronal activity or a pattern of neuronal activity in the animal. By "neuronal stem cell manipulation" is meant that (1) exogenous neuronal stem cells are transplanted into the brain or spinal chord of an animal (2) endogenous neuronal stem cells are stimulated or induced to proliferate in the animal or (3) stem cells which support neuronal cell function.

Methods are provided herein for improving stimulation of neuronal activity or a pattern of neuronal activity, such as that underlying a specific neuronal circuit(s), in an animal comprising treating the animal with an augmenting agent which enhances CREB pathway function in the absence of formal cognitive training. Methods are also provided herein for providing sustained improvement in the stimulation of neuronal activity or a pattern of neuronal activity, such as that underlying a specific neuronal circuit(s), in an animal comprising administering to the animal an augmenting agent which enhances CREB pathway function; and, detecting said sustained improvement. In one embodiment, the method further comprises training the animal under conditions sufficient to stimulate or induce neuronal activity or a pattern of neuronal activity in the animal.

In one embodiment, the invention relates to a method for improving a cognitive deficit associated with age-associated memory impairment in an animal comprising treating the animal with an augmenting agent which enhances CREB pathway function in the absence of formal cognitive training. In another embodiment, the invention relates to a method of providing sustained improvement in a cognitive deficit associated with age-associated memory impairment in an animal comprising administering to the animal an augmenting agent which enhances CREB pathway function; and, detecting said sustained improvement. In one embodiment, the method further comprises training the animal under conditions sufficient to produce a sustained improvement in performance by the animal of a cognitive task whose loss is associated with age-associated memory impairment.

In another embodiment, the invention relates to a method for improving a cognitive deficit associated with a neurodegenerative disease (e.g., Alzheimer's disease, Parkinson's disease, Huntington's disease, other senile dementia) in an animal comprising treating the animal with an augmenting agent which enhances CREB pathway function in the absence of formal cognitive training. In another embodiment, the invention relates to a method of providing sustained improvement in a cognitive deficit associated with a neurodegenerative disease (e.g., Alzheimer's disease, Parkinson's disease, Huntington's disease, other senile dementia) in an animal comprising administering to the animal an augmenting agent which enhances CREB pathway function; and detecting said sustained improvement. In one embodiment, the method further comprises training the animal under conditions sufficient to produce a sustained improvement in performance by the animal of a cognitive task whose deficit is associated with the neurodegenerative disease.

In another embodiment, the invention relates to a method for improving a cognitive deficit associated with a psychiatric disease (e.g., depression, schizophrenia, autism, attention deficit disorder) in an animal comprising treating the animal with an augmenting agent which enhances CREB pathway function in the absence of formal cognitive training. In another embodiment, the invention relates to a method of providing sustained improvement in a cognitive deficit associated with a psychiatric disease (e.g., depression, schizophrenia, autism, attention deficit disorder) in an animal comprising administering to the animal an augmenting agent which enhances CREB pathway function; and detecting said sustained improvement. In one embodiment, the method further comprises training the animal under conditions sufficient to produce an improvement in performance by the animal of a cognitive task whose deficit is associated with the psychiatric disease.

In another embodiment, the invention relates to a method for improving a cognitive deficit associated with trauma dependent loss of cognitive function (e.g., cerebrovascular diseases (e.g., stroke, ischemia), brain tumor, head or brain injury) in an animal comprising treating the animal with an augmenting agent which enhances CREB pathway function in the absence of formal cognitive training. In another embodiment, the invention relates to a method of providing sustained improvement in a cognitive deficit associated with trauma dependent loss of cognitive function (e.g., cerebrovascular diseases (e.g., stroke, ischemia), brain tumor, head or brain injury) in an animal comprising administering to the animal an augmenting agent which enhances CREB pathway function; and detecting said sustained improvement. In one embodiment, the method further comprises training the animal under conditions sufficient to produce a sustained improvement in performance by the animal of a cognitive task whose deficit is associated with trauma dependent loss of cognitive function.

In another embodiment, the invention relates to a method for improving a cognitive deficit associated with a genetic defect (e.g., Rubinstein-Taybi syndrome, down syndrome, Angelman syndrome, neurofibromatosis, Coffin-Lowry syndrome, Rett syndrome, myotonic dystrophy, fragile X syndrome (e.g., fragile X-1, fragile X-2) and William's syndrome) in an animal comprising treating the animal with an augmenting agent which enhances CREB pathway function in the absence of formal cognitive training. Methods are also provided herein for providing sustained improvement in a cognitive deficient associated with a genetic defect in an animal comprising administering to the animal an augmenting agent which enhances CREB pathway function; and detecting said sustained improvement. In one embodiment, the method further comprises training the animal under conditions sufficient to produce an improvement in performance by the animal of a cognitive task whose deficit is associated with a genetic defect.

Methods are provided herein for improving a motor deficit associated with a central nervous system (CNS) disorder or condition in an animal comprising treating the animal with an augmenting agent which enhances CREB pathway function in the absence of formal motor training. Methods are also provided herein for providing sustained improvement in a motor deficit associated with a central nervous system (CNS) disorder or condition in an animal in need of said treatment comprising administering to the animal an augmenting agent which enhances CREB pathway function; and detecting said sustained improvement. In one embodiment, the method further comprises training the animal under conditions sufficient to produce an improvement in performance of a particular motor task by the animal. CNS disorders and conditions include age-associated memory impairment, neurodegenerative diseases (e.g., Alzheimer's disease, Parkinson's disease, Amyotrophic Lateral Sclerosis (ALS or Lou Gehrig's disease), Motor Neuron Disease, Huntington's disease (chorea), other senile dementia), psychiatric diseases (e.g., depression, schizophrenia, autism, attention deficit disorder), trauma dependent loss of function (e.g., cerebrovascular diseases (e.g., stroke, ischemia), brain tumor, head, brain or spinal injury), genetic defects (e.g., Rubinstein-Taybi syndrome, down syndrome, Angelman syndrome, neurofibromatosis, Coffin-Lowry syndrome, Rett syndrome, myotonic dystrophy, fragile X syndrome (e.g., fragile X-1, fragile X-2), William's syndrome) and learning disabilities. It is contemplated that treatment with an augmenting agent which enhances CREB pathway function results in maintained or permanent improvement in performance of the motor task by the animal after administration of the augmenting agent is stopped or discontinued.

It is contemplated that in the various embodiments, the augmenting agent comprises a phosphodiesterase 4 (PDE4) inhibitor. Examples of PDE4 inhibitors include rolipram and compounds of the following formula:

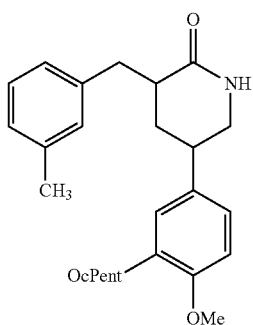

wherein "Me" means "methyl" and "cPent" means "cyclopentyl". It is understood that the above formula embraces both enantimers and mixtures thereof. The compounds can be prepared using the methodology provided in U.S. Pat. No. 6,458,829, the teachings of which are incorporated herein by reference. In a particular embodiment, the 3 and 5 carbons of this above formula are in the S configuration (HT-0712):

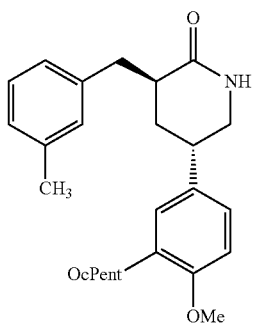

wherein "Me" means "methyl" and "cPent" means "cyclopentyl". Other examples of PDE4 inhibitors can be found in U.S. Publication No. 2002/0028842 A1 (published Mar. 7, 2002); U.S. Pat. No. 6,458,829B1; U.S. Pat. No. 6,525,055B1; U.S. Pat. Nos. 5,552,438 6,436,965; and 6,204,275. Still other PDE4 inhibitors are known and readily available in the art.

BRIEF DESCRIPTION OF THE DRAWING

FIG. 1 is a time course of object recognition (OR) trials. Trial consisted of a single training session followed by a testing session 24 hrs later (except the 4 hr interval for the STM trial). Prior to injury rats had 5 trials to assess pre-injury memory scores. They then received TBI, recovered for 7 days, and began OR rehabilitation as follows: trial 6 post-injury baseline (BS1), trial 7 training with drug (TD1), trial 8, short term memory (STM) test 4 hr interval between training and testing with no drug, trial 9 establish second baseline (BS2), trials 10-14 drug assisted cognitive rehabilitation (drug given before each training session), trial 15 first post-rehab memory assessment (Ass1) no drug at time of training, 1 week of rest, trial 16 second post-rehab memory assessment (Ass2), 5 weeks of rest, trial 17 third post-rehab memory assessment (Ass3), 1 week of rest, trace conditioning training, 1 week of rest, trace conditioning testing.

FIG. 2 shows locomotor rehabilitation on the staggered step. Prior to injury, rats were trained to criteria performance on the staggered step task (A-D, Day 0). All rats were given brain injury and allowed to recover for 7 days. They were tested for the mean number of errors (foot faults) (FIGS. 2A & B) and latency (FIGS. 2C & D) on the staggered step task (Day 1, baseline). All groups had significant increases in the number of foot faults ($p<0.001$). Rats given daily rehabilitation and treatment with the PDE4 inhibitors rolipram (n=11) and HT-0712 (n=13) had fewer foot faults (FIG. 2A) and shorter latencies (FIG. C) then rats given rehabilitation and vehicle treatment (n=11). Rats which were administered the PDE4 inhibitor HT-0712 without staggered step rehabilitation had fewer foot faults (FIG. 2B) and shorter latencies (FIG. 2D) than vehicle treated animals without rehabilitation. (*=$p<0.05$)

FIG. 3 shows object recognition performance (mean DI±S.E.M.). One-day memory retention in object recognition is dependent on long term memory formation. Rats were trained 5 trials prior to injury. Each trial consisted of a 7.5 min training session to a pair of identical objects and a testing session 24 h later to assess long term memory retention. Memory retention was quantified as a discrimination index (see Methods). Prior to injury, rats discriminated between previously explored (old) and novel objects. All pre-injury trials were averaged to obtain a single pre-injury discrimination index (FIG. 3A). There were no significant differences in memory performance between groups which would later receive drug or vehicle treatment (FIG. 3A). Following brain injury and 7 days of recovery, both groups had long term memory deficits for object recognition (FIG. 3B). There were no significant differences between groups for object recognition. Thus, brain injury disrupted normal 24 hr memory for object recognition for all groups prior to treatment (FIG. 3B). For the next trial rats were given either 0.15 mg/kg of HT-0712 or vehicle (i.p.) 20 minutes prior to training. The HT-0712 group showed a preference for the novel object and had a significantly higher discrimination index ($p<0.01$) than the vehicle group (FIG. 3C). In order to determine if brain injury resulted in short term memory deficits, on the next trial rats were trained without drug treatment, but tested after a 4 hr interval, instead of the standard 24 hr interval. Both groups showed a preference for the novel object and there was no significant difference between groups. Therefore, we can conclude that LFP brain injury caused memory deficits for object recognition at 24 hrs but not at 4 hr. (*=$p<0.05$)

FIG. 3E shows object recognition performance in rats prior to injury. One-day memory retention in object recognition is dependent on long term memory formation. Rats were trained for 7.5 min to a pair of identical objects and then tested 24 h later for memory retention. Memory retention was quantified as a discrimination index. This repeated training and testing for memory retention 24 hrs later was repeated for 5 trials prior to injury. During this pre-injury training, rats were not yet assigned to a treatment group and did not receive PDE4 treatment. Prior to injury Student's t test comparing groups revealed no significant differences in object recognition performance on any of the testing days (Trial 1, $p=0.591$; Trial 2, $p=0.177$; Trail 3, $p=0.911$; Trial 4, $p=0.755$; Trial 5, $p=0.780$).

FIG. 4 shows drug assisted cognitive rehabilitation performance (mean DI±SEM). On the first day of repeated cognitive rehabilitation, rats were tested for a second time without drug or vehicle injection (FIG. 4A, trial 0). There was no significant difference between vehicle and HT-0712 groups on this second baseline assessment. Rats then began daily drug assisted cognitive rehabilitation with HT-0712 or vehicle for 5 trials (FIG. 4A, trial 1-5). On rehab trial 1

(p=0.001), trial 2 (p=0.001), trial 3 (p=0.007), and trial 5 (p=0.001) the HT-0712 group performed significantly better than the vehicle group. To assess if drug assisted rehab improved memory performance without drug, rats were trained/tested without drug treatment. The group receiving HT-0712 assisted cognitive rehabilitation performed significantly better that the vehicle group (FIG. 4B). In order to determine if this amelioration of long term memory deficits was due to a sub-acute effect of repeated HT-0712 administration, rats rested for 1 week before being tested again for long term memory function without drug (FIG. 4C). Again the effect of PDE4 assisted cognitive rehabilitation persisted. The HT-0712 group performed significantly better than the vehicle treated group. (*=p<0.05)

FIG. 5 shows long lasting effects of cognitive rehabilitation: To determine if the improvement in memory function following PDE4 assisted cognitive rehabilitation was long lasting, rats were tested for object recognition performance 8 weeks following the end of rehabilitation (FIG. 5A). The PDE4 assisted rehab group performed significantly better than the vehicle treated group. Rats were then rats were then tested for 1 week memory retention for trace fear conditioning. Again the PDE4 assisted cognitive rehab group performed significantly better than the vehicle treated group. (FIG. 5B). (*=p<0.05) The improved memory function translated to another hippocampal dependant memory task.

FIG. 5C shows memory performance for trace fear conditioning in motor-rehabilitation animals. To determine if the improvement in motor performance (motor memory) in PDE4 assisted drug rehabilitation groups was specific to motor performance, or if it translated to improved cognitive performance for trace fear memory, rats were trained for trace fear memory 1 week after the end of motor rehabilitation. Rats were tested for trace fear memory one week following training. There were no significant differences between any of the PDE4/rehabilitation/no rehabilitation groups.

DETAILED DESCRIPTION OF THE INVENTION

For many tasks in many species, including human, spaced training protocols (multiple training sessions with a rest interval between each) produce stronger, longer-lasting memory than massed training protocols (multiple training sessions with no rest interval in between).

Behavior-genetic studies of Pavlovian olfactory learning in Drosophila have established that massed training produces a long-lasting memory that nevertheless decays away in at least four days, is not protein synthesis-dependent, is not disrupted by overexpression of a CREB-repressor transgene, and is disrupted in radish mutants (Tully, T. et al., Cell, 79(1):35-47 (1994); and Yin, J. C. et al., Cell, 79(1):49-58 (1994)). In contrast, spaced training produces a long-lasting memory that persists for at least seven days, is protein synthesis-dependent, is disrupted by overexpression of a CREB-repressor transgene and is normal in radish mutants (Tully, T. et al., Cell, 79(1):35-47 (1994); and Yin, J. C. et al., Cell, 79(1):49-58 (1994)). One day after spaced training, memory retention is composed of both the protein synthesis- and CREB-independent early memory (ARM) and the protein synthesis- and CREB-dependent long-term memory (LTM). Additional massed training is insufficient to induce LTM (Tully, T. et al., Cell, 79(1):35-47 (1994); and Yin, J. C. et al., Cell, 79(1):49-58 (1994)).

A growing body of evidence extends these results from invertebrates to mammals. For example, in Aplysia, molecular manipulations of CREB expression, similar to those in flies, suppress or enhance (i) LTM of a facilitatory electrophysiological response at a sensorimotor monosynapse in cell culture and (ii) the synaptic connections between sensory and motor neurons that are normally produced after spaced applications of the facilitatory stimulus (Bartsch, D. et al., Cell, 83(6):979-992 (1995)). In rats, injections of antisense RNA oligonucleotides into hippocampus or amygdala block LTM formation of two different tasks that are dependent on activity in these anatomical regions, respectively (Guzowski, J. F. et al., Proc. Natl. Acad. Sci. USA, 94(6):2693-2698 (1997); and Lamprecht, R. et al., J. Neurosci., 17(21):8443-8450 (1997)). In mice, LTM formation for both implicit and explicit tasks is defective in CREB mutant mice (Bourtchuladze, R. et al., Cell, 79(1):59-68 (1994)).

Training of transgenic mice, carrying a CRE-dependent reporter gene (beta-galactosidase), in hippocampal-dependent contextual fear conditioning or passive avoidance tasks induces CRE-dependent reporter gene expression in areas CA1 and CA3 of the hippocampus. Training of these mice in an amygdala-dependent fear conditioning task induces CRE-dependent reporter gene expression in the amygdala, but not the hippocampus. Thus, training protocols that induce LTM formation also induce CRE-dependent gene transcription in specific anatomical areas of the mammalian brain (Impey, S. et al., Nat. Neurosci., 1(7):595-601 (1998)).

With these animal models, three salient cases of LTM enhancement have been demonstrated. First, overexpression of a CREB-activator transgene abrogates the requirements for multiple, spaced training sessions and, instead, induces LTM formation after only one training session (which normally produces little or no memory retention 24 hours later (Yin, J. C. et al., Cell, 81(1):107-115 (1995)). Second, injection of a virally expressed CREB-activator transgene into rat amygdala also is sufficient to enhance memory after massed training for the fear-potentiated startle response, which abrogates the requirement for a rest interval in spaced training (Josselyn, S. A. et al., Society for Neuroscience, Vol. 24, Abstract 365.10 (1998); and Josselyn, S. A. et al., J. Neurosci., 21:2404-2412 (2001)). Third, LTM formation in CREB-deficient mice (Bourtchuladze, R. et al., Cell, 79(1): 59-68 (1994)) can form normally, if mutant mice are subjected to a different, spaced training protocol (Kogan, J. H. et al., Curr. Biol., 7(1):1-11 (1997)).

CREB also appears involved in various forms of developmental and cellular plasticity in the vertebrate brain. For example, neuronal activity increases CREB activity in the cortex (Moore, A. N. et al., J. Biol. Chem., 271(24):14214-14220 (1996)). CREB also mediates developmental plasticity in the hippocampus (Murphy, D. D. et al., Proc. Natl. Acad. Sci. USA, 94(4):1482-1487 (1997)), in the somatosensory cortex (Glazewski, S. et al., Cereb. Cortex, 9(3): 249-256 (1999)), in the striatum (Liu, F. C. et al., Neuron, 17(6):1133-1144 (1996)), and in the visual cortex (Pham, T. A. et al., Neuron, 22(1):63-72 (1999)).

CREB appears to be affected in human neurodegenerative disease and brain injury. For example, CREB activation and/or expression is disrupted in Alzheimer's disease (Ikezu, T. et al., EMBO J., 15(10):2468-2475 (1996); Sato, N. et al., Biochem. Biophys. Res. Commun., 232(3):637-642 (1997); Yamamoto-Sasaki, M. et al., Brain. Res., 824(2):300-303 (1999); Vitolo, O. V. et al., Proc. Natl. Acad. Sci. USA, 13217-13221 (2002)). CREB activation and/or expression is also elevated after seizures or ischemia (Blendy, J. A. et al., Brain Res., 681(1-2):8-14 (1995); and Tanaka, K. et al., Neuroreport, 10(11):2245-2250 (1999)). "Environmental enrichment" is neuroprotective, preventing cell death by acting through CREB (Young, D. et al., Nat. Med., 5(4): 448-453 (1999)).

CREB functions during drug sensitivity and withdrawal. For example, CREB is affected by ethanol (Pandey, S. C. et al., Alcohol Clin. Exp. Res., 23(9):1425-1434 (1999); Constantinescu, A. et al., J. Biol. Chem., 274(38):26985-26991 (1999); Yang, X. et al., Alcohol Clin. Exp. Res., 22(2):382-390 (1998); Yang, X. et al., J. Neurochem., 70(1):224-232 (1998); and Moore, M. S. et al., Cell, 93(6):997-1007 (1998)), by cocaine (Carlezon, W. A., Jr. et al., Science, 282(5397):2272-2275 (1998)), by morphine (Widnell, K. L. et al., J. Pharmacol. Exp. Ther., 276(1):306-315 (1996)), by methamphetamine (Muratake, T. et al., Ann N.Y. Acad. Sci., 844:21-26 (1998)) and by cannabinoid (Calandra, B. et al., Eur. J. Pharmacol., 374(3):445-455 (1999); and Herring, A. C. et al., Biochem. Pharmacol., 55(7): 1013-1023 (1998)).

A signal transduction pathway that can stimulate the CREB/CRE transcriptional pathway is the cAMP regulatory system. Consistent with this, mice lacking both adenylate cyclase 1 (AC1) and AC8 enzymes fail to learn (Wong S. T. et al., Neuron, 23(4):787-798 (1999)). In these mice, administration of forskolin to area CA1 of the hippocampus restores learning and memory of hippocampal-dependent tasks. Furthermore, treatment of aged rats with drugs that elevate cAMP levels (such as rolipram and D1 receptor agonists) ameliorates an age-dependent loss of hippocampal-dependent memory and cellular long-term potentiation (Barad, M. et al., Proc. Natl. Acad. Sci. USA, 95(25):15020-15025 (1998)). These latter data suggest that a cAMP signaling is defective in learning-impaired aged rats (Bach, M. E. et al., Proc. Natl. Acad. Sci. USA, 96(9):5280-5285 (1999)).

The present invention relates to a novel methodology, which can (1) rehabilitate various forms of cognitive dysfunction or (2) enhance normal cognitive performance. Administration of a CREB pathway enhancing drug acts via a general molecular mechanism of synaptic plasticity, which apparently converts the biochemical effect of a newly acquired experience into a long-lasting structural change of the synapse. Administration of a CREB pathway enhancing drug can be applied for any aspect of brain function that shows a lasting performance gain after cognitive training. Accordingly, administration of a CREB pathway enhancing drug can be used in rehabilitating an animal with any form of cognitive or motor dysfunction or in enhancing or improving any aspect of normal cognitive or motor performance in an animal.

A growing body of evidence suggests that neurons continue to proliferate in the adult brain (Arsenijevic, Y. et al., Exp. Neurol., 170: 48-62 (2001); Vescovi, A. L. et al., Biomed. Pharmacother., 55:201-205 (2001); Cameron, H. A. and McKay, R. D., J. Comp. Neurol., 435:406-417 (2001); and Geuna, S. et al., Anat. Rec., 265:132-141 (2001)) and that such proliferation is in response to various experiences (Nilsson, M. et al., J. Neurobiol., 39:569-578 (1999); Gould, E. et al., Trends Cogn. Sci., 3:186-192 (1999); Fuchs, E. and Gould, E., Eur. J. Neurosci., 12: 2211-2214 (2000); Gould, E. et al., Biol. Psychiatry, 48:715-720 (2000); and Gould, E. et al., Nat. Neurosci., 2:260-265 (1999)). Experimental strategies now are underway to transplant neuronal stem into adult brain for various therapeutic indications (Kurimoto, Y. et al., Neurosci. Lett., 306:57-60 (2001); Singh, G., Neuropathology, 21:110-114 (2001); and Cameron, H. A. and McKay, R. D., Nat. Neurosci., 2:894-897 (1999)). Much already is known about neurogenesis in embryonic stages of development (Saitoe, M. and Tully, T., "Making connections between synaptic and behavioral plasticity in Drosophila", In Toward a Theory of Neuroplasticity, J. McEachem and C. Shaw, Eds. (New York: Psychology Press), pp. 193-220 (2000)). Neuronal differentiation, neurite extension and initial synaptic target recognition all appear to occur in an activity-independent fashion. Subsequent synaptogenesis and synaptic growth, however, then requires ongoing neuronal activity to fine-tune synaptic connections in a functionally relevant manner. These findings suggest that functional (final) integration of transplanted neural stem cells require neuronal activity. Thus, administration of a CREB pathway enhancing drug can be used to exercise appropriate neuronal circuits to fine-tune the synaptic connections of newly acquired, transplanted stem cells that differentiate into neurons. By "exercise appropriate neuronal circuit(s)" is meant the induction in the appropriate neuronal circuit(s) of a pattern of neuronal activity, which corresponds to that produced by a particular cognitive training protocol. The cognitive training protocol can be used to induce such neuronal activity. Alternatively, neuronal activity can be induced by direct electrical stimulation of the neuronal circuitry. "Neuronal activity" and "neural activity" are used interchangeably herein.

ACT comprises a specific training protocol for each brain function and a general administration of CREB pathway-enhancing drugs. The training protocol (cognitive training) induces neuronal activity in specific brain regions and produces improved performance of a specific brain (cognitive) function. CREB pathway-enhancing drugs, also referred to herein as augmenting agents, enhance CREB pathway function, which is required to consolidate newly acquired information into LTM. By "enhance CREB pathway function" is meant the ability to enhance or improve CREB-dependent gene expression. CREB-dependent gene expression can be enhanced or improved by increasing endogenous CREB production, for example by directly or indirectly stimulating the endogenous gene to produce increased amounts of CREB, or by increasing functional (biologically active) CREB. See, e.g., U.S. Pat. Nos. 5,929, 223; 6,051,559; and International Publication No. WO9611270 (published Apr. 18, 1996), which references are incorporated herein in their entirety by reference. Administration of CREB pathway-enhancing drugs decreases the training needed to yield a performance gain relative to that yielded with training alone. In particular, ACT can enhance cognitive training by reducing the number of training sessions required to yield a performance gain relative to that yielded with cognitive training alone or by requiring shorter or no rest intervals between training sessions to yield a performance gain. In this manner, ACT can improve the efficiency of cognitive training techniques, thereby yielding significant economic benefit. By "performance gain" is meant an improvement in an aspect of cognitive performance.

The invention provides methods for enhancing a specific aspect of cognitive performance in an animal (particularly in a human or other mammal or vertebrate) in need thereof comprising (a) administering to the animal an augmenting agent which enhances CREB pathway function; and optionally (b) training the animal under conditions sufficient to produce an improvement in performance of a particular cognitive task by the animal.

For example, formal cognitive training protocols are employed in treating patients with depression (monopolar) and/or phobias to help them unlearn pathological responses associated with the depression and/or phobia(s) and learn appropriate behavior. Administration of a CREB pathway-enhancing drug optionally in conjunction with cognitive training reduces the time and/or number of training sessions required to yield a gain in performance in these patients. As such, overall treatment is accomplished in a shorter period of time.

Similarly, formal cognitive training protocols are employed in treating patients with autism to help them unlearn pathological responses and to learn appropriate behavior. Administration of a CREB pathway-enhancing drug optionally in conjunction with cognitive training reduces the time and/or number of training sessions required to yield a gain in performance in these patients.

Formal cognitive training protocols (e.g., physical therapy, bio-feedback methods) are employed in rehabilitating stroke patients (stroke rehabilitation), particularly rehabilitating impaired or lost sensory-motor function(s). Administration of a CREB pathway-enhancing drug in conjunction with cognitive training reduces the time and/or number of training sessions required to yield a gain in performance in these patients. Faster and more efficient recovery of lost cognitive or motor function(s) are expected as a result.

Formal cognitive training protocols (e.g., massed training, spaced training) are employed in learning a new language or in learning to play a new musical instrument. Administration of a CREB pathway-enhancing drug in conjunction with cognitive training reduces the time and/or number of training sessions required to yield a gain in performance. As a result, less practice (training sessions) is required to learn the new language or to learn to play the new musical instrument.

Formal cognitive training protocols are employed in improving learning and/or performance in individuals with learning, language or reading disabilities. Administration of a CREB pathway-enhancing drug in conjunction with cognitive training reduces the time and/or number of training sessions required to yield a gain in performance in these individuals.

Formal cognitive training protocols are employed to exercise neuronal circuits in individuals to fine-tune synaptic connections of newly acquired, transplanted stem cells that differentiate into neurons. Administration of a CREB pathway-enhancing drug in conjunction with cognitive training reduces the time and/or number of training sessions required for the induction in (a) specific neuronal circuit(s) of a pattern of neuronal activity in these individuals.

Formal cognitive training protocols are employed for repeated stimulation of neuronal activity or a pattern of neuronal activity underlying (a) specific neuronal circuit(s) in individuals. Administration of a CREB pathway-enhancing drug in conjunction with cognitive training reduces the time and/or number of training sessions and/or underlying pattern of neuronal activity required to induce CREB-dependent long-term structure/function (i.e., long-lasting) change among synaptic connections of the neuronal circuit.

Intensive rehabilitation therapy can improve functional recovery after brain injury. This recovery occurs through the reorganization of residual brain tissue when surviving neurons are 'retrained' to assume lost function. Changes in neural plasticity are believed to underlie this reorganization. Activation of the cAMP/CREB pathway is an essential step for experience-dependent changes in neural plasticity. The effects of HT-0712 and Rolipram on motor and cognitive rehabilitation following lateral fluid percussion (LFP) brain injury were examined. Adult rats were trained to a criterion performance on a skilled motor task (the staggered step) and injured using the LFP device. After one week of recovery, rats began skilled motor rehabilitation with either PDE4 inhibitors or vehicle. Both HT-0712 and Rolipram significantly enhanced motor rehabilitation. In a separate group of animals, rats were first tested for baseline memory performance for object recognition. Following injury, rats showed intact object recognition at 4 hours after training, but deficient memory at 24 hours. HT-0712 or vehicle was given during repeated cognitive training for object recognition (cognitive rehab). After 6 sessions of rehab, the HT-0712 group performed significantly better than the vehicle group. This memory improvement lasted for as long as eight weeks in the absence of drug and translated to improved memory performance for trace fear conditioning. Surprisingly, the PDE4 inhibitor HT-0712 may be used to improve motor and cognitive recovery following brain injury.

Training can comprise one or multiple training sessions and is training appropriate to produce an improvement in performance of the cognitive task of interest. For example, if an improvement in language acquisition is desired, training would focus on language acquisition. If an improvement in ability to learn to play a musical instrument is desired, training would focus on learning to play the musical instrument. If an improvement in a particular motor skill is desired, training would focus on acquisition of the particular motor skill. The specific cognitive task of interest is matched with appropriate training.

The invention also provides methods for repeated stimulation of neuronal activity or a pattern of neuronal activity, such as that underlying a specific neuronal circuit(s), in an animal comprising (a) administering to the animal an augmenting agent which enhances CREB pathway function; and (b) training the animal under conditions sufficient to stimulate or induce neuronal activity or a pattern of neuronal activity in the animal. In this case, training is training appropriate to stimulate or induce neuronal activity or a pattern of neuronal activity in the animal.

By "multiple training sessions" is meant two or more training sessions. The augmenting agent can be administered before, during or after one or more of the training sessions. In a particular embodiment, the augmenting agent is administered before and during each training session. Treatment with augmenting agent in connection with each training session is also referred to as the "augmenting treatment". By "training" is meant cognitive training.

Formal cognitive training protocols are known and readily available in the art. See for example, Karni, A. and Sagi, D., "Where practice makes perfect in text discrimination: evidence for primary visual cortex plasticity", Proc. Natl. Acad. Sci. USA, 88:4966-4970 (1991); Karni, A. and Sagi, D., "The time course of learning a visual skill", Nature, 365: 250-252 (1993); Kramer, A. F. et al., "Task coordination and aging: explorations of executive control processes in the task switching paradigm", Acta Psychol. (Amst), 101:339-378 (1999); Kramer, A. F. et al., "Training for executive control: Task coordination strategies and aging", In Aging and Skilled Performance: Advances In Theory and Applications, W. Rogers et al., eds. (Hillsdale, N.J.: Erlbaum) (1999); Rider, R. A. and Abdulahad, D. T., "Effects of massed versus distributed practice on gross and fine motor proficiency of educable mentally handicapped adolescents", Percept. Mot. Skills, 73:219-224 (1991); Willis, S. L. and Schaie, K. W., "Training the elderly on the ability factors of spatial orientation and inductive reasoning", Psychol. Aging, 1:239-247 (1986); Willis, S. L. and Nesselroade, C. S., "Long-term effects of fluid ability training in old-old age", Develop. Psychol., 26:905-910 (1990); Wek, S. R. and Husak, W. S., "Distributed and massed practice effects on motor performance and learning of autistic children", Percept. Mot.

Skills, 68:107-113 (1989); Verhaehen, P. et al., "Improving memory performance in the aged through mnemonic training: a meta-analytic study", Psychol. Aging, 7:242-251 (1992); Verhaeghen, P. and Salthouse, T. A., "Meta-analyses of age-cognition relations in adulthood: estimates of linear and nonlinear age effects and structural models", Psychol. Bull., 122:231-249 (1997); Dean, C. M. et al., "Task-related circuit training improves performance of locomotor tasks in chronic stroke: a randomized, controlled pilot trial", Arch. Phys. Med. Rehabil., 81:409-417 (2000); Greener, J. et al., "Speech and language therapy for aphasia following stroke", Cochrane Database Syst. Rev., CD000425 (2000); Hummelsheim, H. and Eickhof, C., "Repetitive sensorimotor training for arm and hand in a patient with locked-in syndrome", Scand. J. Rehabil. Med., 31:250-256 (1999); Johansson, B. B., "Brain plasticity and stroke rehabilitation. The Willis lecture", Stroke, 31:223-230 (2000); Ko Ko, C., "Effectiveness of rehabilitation for multiple sclerosis", Clin. Rehabil., 13 (Suppl. 1):33-41 (1999); Lange, G. et al., "Organizational strategy influence on visual memory performance after stroke: cortical/subcortical and left/right hemisphere contrasts", Arch. Phys. Med. Rehabil., 81:89-94 (2000); Liepert, J. et al., "Treatment-induced cortical reorganization after stroke in humans", Stroke, 31:1210-1216 (2000); Lotery, A. J. et al., "Correctable visual impairment in stroke rehabilitation patients", Age Ageing, 29:221-222 (2000); Majid, M. J. et al., "Cognitive rehabilitation for memory deficits following stroke" (Cochrane review), Cochrane Database Syst. Rev., CD002293 (2000); Merzenich, M. et al., "Cortical plasticity underlying perceptual, motor, and cognitive skill development: implications for neurorehabilitation", Cold Spring Harb. Symp. Quant. Biol., 61:1-8 (1996); Merzenich, M. M. et al., "Temporal processing deficits of language-learning impaired children ameliorated by training", Science, 271:77-81 (1996); Murphy, E., "Stroke rehabilitation", J. R. Coll. Physicians Lond., 33:466-468 (1999); Nagarajan, S. S. et al., "Speech modifications algorithms used for training language learning-impaired children", IEEE Trans. Rehabil. Eng., 6:257-268. (1998); Oddone, E. et al., "Quality Enhancement Research Initiative in stroke: prevention, treatment, and rehabilitation", Med. Care 38:192-1104 (2000); Rice-Oxley, M. and Turner-Stokes, L., "Effectiveness of brain injury rehabilitation", Clin. Rehabil., 13(Suppl 1):7-24 (1999); Tallal, P. et al., "Language learning impairments: integrating basic science, technology, and remediation", Exp. Brain Res., 123: 210-219 (1998); Tallal, P. et al., "Language comprehension in language-learning impaired children improved with acoustically modified speech", Science, 271:81-84 (1996); Wingfield, A. et al., "Regaining lost time: adult aging and the effect of time restoration on recall of time-compressed speech", Psycho. Aging, 14:380-389 (1999), which references are incorporated herein in their entirety by reference.

As used herein, the term "animal" includes mammals, as well as other animals, vertebrate and invertebrate (e.g., birds, fish, reptiles, insects (e.g., Drosophila species), mollusks (e.g., Aplysia). The terms "mammal" and "mammalian", as used herein, refer to any vertebrate animal, including monotremes, marsupials and placental, that suckle their young and either give birth to living young (eutharian or placental mammals) or are egg-laying (metatharian or non-placental mammals). Examples of mammalian species include humans and primates (e.g., monkeys, chimpanzees), rodents (e.g., rats, mice, guinea pigs) and ruminants (e.g., cows, pigs, horses).

The animal can be an animal with some form and degree of cognitive dysfunction or an animal with normal cognitive performance (i.e., an animal without any form of cognitive failure (dysfunction or loss of any cognitive function)).

Cognitive dysfunction, commonly associated with brain dysfunction and central nervous system (CNS) disorders or conditions, arises due to heredity, disease, injury and/or age. CNS disorders and conditions associated with some form and degree of cognitive failure (dysfunction) include, but are not limited to the following:

1) age-associated memory impairment;
2) neurodegenerative disorders, such as delirium (acute confusional state); dementia, including Alzheimer's disease and non-Alzheimer's type dementias, such as, but not limited to, Lewy body dementia, vascular dementia, Binswanger's dementia (subcortical arteriosclerotic encephalopathy), dementias associated with Parkinson's disease, progressive supranuclear palsy, Huntington's disease (chorea), Pick's disease, normal-pressure hydrocephalus, Creutzfeldt-Jakob disease, Gerstmann-Strussler-Scheinker disease, neurosyphilis (general paresis) or HIV infection, frontal lobe dementia syndromes, dementias associated with head trauma, including dementia pugilistica, brain trauma, subdural hematoma, brain tumor, hypothyroidism, vitamin $B_{12}$ deficiency, intracranial radiation; other neurodegenerative disorders;
3) psychiatric disorders, including affective disorders (mood disorders), such as, but not limited to, depression, including depressive pseudodementia; psychotic disorders, such as, but not limited to, schizophrenia and autism (Kanner's Syndrome); neurotic disorders, such as, but not limited to, anxiety and obsessive-compulsive disorder; attention deficit disorder;
4) trauma-dependent loss of cognitive function, such as, but not limited to that associated with (due to), cerebrovascular diseases, including stroke and ischemia, including ischemic stroke; brain trauma, including subdural hematoma and brain tumor; head injury, complications from Coronary Artery Bypass Graft (CABG) surgery and neurotoxicity, excitotoxicity, and seizures;
5) disorders associated with some form and degree of cognitive dysfunction arising due to a genetic defect, such as, but not limited to, Rubinstein-Taybi syndrome, down syndrome, Angelman syndrome, fragile X syndrome (fragile X-1, fragile X-2), neurofibromatosis, Coffin-Lowry syndrome, myotonic dystrophy, Rett syndrome, William's syndrome, Klinefelter's syndrome, mosaicisms, trisomy 13 (Patau's syndrome), trisomy 18 (Edward's syndrome), Turner's syndrome, cri du chat syndrome, Lesch-Nyhan syndrome (hyperuricemia), Hunter's syndrome, Lowe's oculocerebrorenal syndrome, Gaucher's disease, Hurler's syndrome (mucopolysaccharidosis), Niemann-Pick disease, Tay-Sachs disease, galactosemia, maple syrup urine disease, phenylketonuria, aminoacidurias, acidemias, tuberous sclerosis and primary microcephaly;
6) learning, language or reading disabilities, particularly in children. By "learning disabilities" is meant disorders of the basic psychological processes that affect the way an individual learns. Learning disabilities can cause difficulties in listening, thinking, talking, reading, writing, spelling, arithmetic or combinations of any of the foregoing. Learning disabilities include perceptual handicaps, dyslexia and developmental aphasia.

The terms "cognitive performance" and "cognitive function" are art-recognized terms and are used herein in accordance with their art-accepted meanings. By "cognitive task" is meant a cognitive function. Cognitive functions include memory acquisition, visual discrimination, auditory discrimination, executive functioning, motor skill learning, abstract reasoning, spatial ability, speech and language skills and language acquisition. By "enhance a specific aspect of cognitive performance" is meant the ability to enhance or improve a specific cognitive or brain function, such as, for example, the acquisition of memory or the performance of a learned task. By "improvement in performance of a particular cognitive task" is meant an improvement in performance of a specific cognitive task or aspect of brain function relative to performance prior to training. For example, if after a stroke, a patient can only wiggle his or her toe, an improvement in performance (performance gain) in the patient would be the ability to walk, for example.

'Providing sustained improvement" means that the improvement in performance of a particular cognitive task remains after administration of the augmenting agent is stopped.

Accordingly, the invention also relates to methods of improving a cognitive deficit associated with a CNS disorder or condition in an animal (particularly in a human or other mammal or vertebrate) comprising treating the animal with an augmenting agent which enhances CREB pathway function in the absence of formal cognitive training. The invention also relates to methods for providing sustained improvement in a cognitive deficit associated with a CNS disorder or condition in an animal (particularly in a human or other mammal or vertebrate) comprising administering to the animal an augmenting agent which enhances CREB pathway function and detecting the sustained improvement. The invention also relates to methods further comprising training the animal under conditions sufficient to produce an improvement in performance of a particular cognitive task by the animal.

In one embodiment, the invention relates to a method of treating a cognitive deficit associated with age-associated memory impairment in an animal in need of said treatment comprising (a) administering to the animal an augmenting agent which enhances CREB pathway function; and optionally (b) training the animal under conditions sufficient to produce an improvement in performance by the animal of a cognitive task whose loss is associated with age-associated memory impairment.

In particular embodiments, the augmenting agent is a phosphodiesterase 4 (PDE4) inhibitor. Examples of PDE4 inhibitors include rolipram and compounds of the following formula:

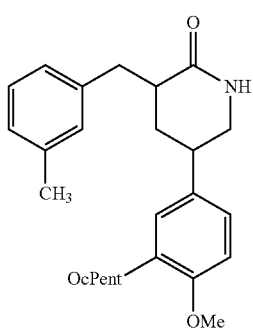

wherein "Me" means "methyl" and "cPent" means "cyclopentyl". It is understood that the above formula embraces both enantimers and mixtures thereof. The compounds can be prepared using the methodology provided in U.S. Pat. No. 6,458,829, the teachings of which are incorporated herein by reference. In a particular embodiment, the 3 and 5 carbons of this above formula are in the S configuration:

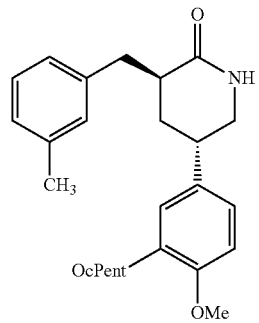

wherein "Me" means "methyl" and "cPent" means "cyclopentyl". Other examples of PDE4 inhibitors can be found in U.S. Publication No. 2002/0028842 A1 (published Mar. 7, 2002); U.S. Pat. Nos. 6,458,829B1; 6,525,055B1; ,552,438; 6,436,965; and 6,204,275. Still other PDE4 inhibitors are known and readily available in the art.

Mental retardation impacts cognitive processing and cognitive functions, including learning and memory acquisition (Weeber, E. J. et al., Neuron, 33:845-848)). Mental retardation may be caused by chromosomal or genetic factors, congenital infections, teratogens (drugs and other chemicals), malnutrition, radiation or unknown conditions affecting implantation and embryogenesis. Mental retardation syndromes include, but are not limited to, Klinefelter's syndrome, mosaicisms, trisomy 13 (Patau's syndrome), trisomy 18 (Edward's syndrome), Turner's syndrome, cri du chat syndrome, Lesch-Nyhan syndrome (hyperuricemia), Hunter's syndrome, Lowe's oculocerebrorenal syndrome, Gaucher's disease, Hurler's syndrome (mucopolysaccharidosis), Niemann-Pick disease, Tay-Sachs disease, galactosemia, maple syrup urine disease, phenylketonuria, aminoacidurias, acidemias, tuberous sclerosis and primary microcephaly. Mental retardation syndromes also include Rubinstein-Taybi syndrome, down syndrome, Angelman syndrome, neurofibromatosis, Coffin-Lowry syndrome, Rett syndrome, myotonic dystrophy, fragile X syndrome (e.g., fragile X-1, fragile X-2) and William's syndrome (Weeber, E. J. et al., Neuron, 33:845-848 (2002)).

The invention also relates to methods of therapy of a cognitive deficit associated with a CNS disorder or condition in an animal having undergone neuronal stem cell manipulation comprising (a) administering to the animal an augmenting agent which enhances CREB pathway function; and (b) training the animal under conditions sufficient to stimulate or induce neuronal activity or a pattern of neuronal activity in the animal. By "neuronal stem cell manipulation" is meant that (1) exogenous neuronal stem cells are transplanted into the brain or spinal chord of an animal or (2) endogenous neuronal stem cells are stimulated or induced to proliferate in the animal. Methods of transplanting neuronal stem cells into the brain or spinal chord of an animal are known and readily available in the art (see, e.g., Cameron, H. A. and McKay, R. D., Nat. Neurosci., 2:894-897 (1999); Kurimoto, Y. et al., Neurosci. Lett., 306:57-60 (2001); and Singh, G., Neuropathology, 21:110-114 (2001)). Methods of stimulating or inducing proliferation of endogenous neuronal stem cells in an animal are known and readily available in the art (see, e.g., Gould, E. et al., Trends Cogn. Sci, 3:186-192 (1999); Gould, E. et al., Biol. Psychiatry, 48:715-20 (2000); Nilsson, M. et al, J. Neurobiol., 39:569-578 (1999); Fuchs, E. and Gould, E., Eur. J Neurosci., 12:2211-2214 (2000); and Gould, E. et al., Nat. Neurosci., 2:260-265 (1999)). The particular methods of transplanting neuronal stem cells into the brain or spinal chord of an animal and the particular methods of stimulating or inducing proliferation of endogenous neuronal stem cells in an animal are not critical to the practice of the invention.

The invention further relates to methods of improving or enhancing learning and/or performance in an animal with a learning, language or reading disability, or combinations of any of the foregoing, comprising (a) administering to the animal an augmenting agent which enhances CREB pathway function; and (b) training the animal under conditions sufficient to produce an improvement in performance by the animal of a cognitive task associated with the disability in learning, language or reading performance.

Augmenting agents, as used herein, are compounds with pharmacological activity and include drugs, chemical compounds, ionic compounds, organic compounds, organic ligands, including cofactors, saccharides, recombinant and synthetic peptides, proteins, peptoids, nucleic acid sequences, including genes, nucleic acid products, and other molecules and compositions.

For example, augmenting agents can be cell permeant cAMP analogs (e.g, 8-bromo cAMP); activators of adenylate cyclase 1 (AC1) (e.g., forskolin); agents affecting G-protein linked receptor, such as, but not limited to adrenergic receptors and opioid receptors and their ligands (e.g., phenethylamines); modulators of intracellular calcium concentration (e.g., thapsigargin, N-methyl-D-aspartate (NMDA) receptor agonists); inhibitors of the phosphodiesterases responsible for cAMP breakdown (e.g., phosphodiesterase 1 (PDE1) inhibitors (e.g., iso-buto-metho-xanthine (IBMX)), phosphodiesterase 2 (PDE2) inhibitors (e.g., iso-buto-metho-xanthine (IBMX)), phosphodiesterase 3 (PDE3) inhibitors, phosphodiesterase 4 (PDE4) inhibitors (e.g., rolipram, HT0712), etc.) (see also, e.g., U.S. Pat. No. 6,458,829B1; U.S. Publication No. 2002/0028842A1 (published Mar. 7, 2002)); and modulators of protein kinases and protein phosphatases, which mediate CREB protein activation and CREB-dependent gene expression. Augmenting agents can be exogenous CREB, CREB analogs, CREB-like molecules, biologically active CREB fragments, CREB fusion proteins, nucleic acid sequences encoding exogenous CREB, CREB analogs, CREB-like molecules, biologically active CREB fragments or CREB fusion proteins.

Augmenting agents can also be CREB function modulators, or nucleic acid sequences encoding CREB function modulators. CREB function modulators, as used herein, have the ability to modulate CREB pathway function. By "modulate" is meant the ability to change (increase or decrease) or alter CREB pathway function.

Augmenting agents can be compounds which are capable of enhancing CREB function in the CNS. Such compounds include, but are not limited to, compounds which affect membrane stability and fluidity and specific immunostimulation. In a particular embodiment, the augmenting agent is capable of transiently enhancing CREB pathway function in the CNS.

CREB analogs, or derivatives, are defined herein as proteins having amino acid sequences analogous to endogenous CREB. Analogous amino acid sequences are defined herein to mean amino acid sequences with sufficient identity of amino acid sequence of endogenous CREB to possess the biological activity of endogenous CREB, but with one or more "silent" changes in the amino acid sequence. CREB analogs include mammalian CREM, mammalian ATF-1 and other CREB/CREM/ATF-1 subfamily members.

CREB-like molecule, as the term is used herein, refers to a protein which functionally resembles (mimics) CREB. CREB-like molecules need not have amino acid sequences analogous to endogenous CREB.

Biologically active polypeptide fragments of CREB can include only a part of the full-length amino acid sequence of CREB, yet possess biological activity. Such fragments can be produced by carboxyl or amino terminal deletions, as well as internal deletions.

Fusion proteins comprise a CREB protein as described herein, referred to as a first moiety, linked to a second moiety not occurring in the CREB protein. The second moiety can be a single amino acid, peptide or polypeptide or other organic moiety, such as a carbohydrate, a lipid or an inorganic molecule.

Nucleic acid sequences are defined herein as heteropolymers of nucleic acid molecules. The nucleic acid molecules can be double stranded or single stranded and can be a deoxyribonucleotide (DNA) molecule, such as cDNA or genomic DNA, or a ribonucleotide (RNA) molecule. As such, the nucleic acid sequence can, for example, include one or more exons, with or without, as appropriate, introns, as well as one or more suitable control sequences. In one example, the nucleic acid molecule contains a single open reading frame which encodes a desired nucleic acid product. The nucleic acid sequence is "operably linked" to a suitable promoter.

A nucleic acid sequence encoding a desired CREB protein, CREB analog (including CREM, ATF-1), CREB-like molecule, biologically active CREB fragment, CREB fusion protein or CREB function modulator can be isolated from nature, modified from native sequences or manufactured de novo, as described in, for example, Ausubel et al., Current Protocols in Molecular Biology, John Wiley & Sons, New York (1998); and Sambrook et al., Molecular Cloning: A Laboratory Manual, 2nd edition, Cold Spring Harbor University Press, New York. (1989). Nucleic acids can be isolated and fused together by methods known in the art, such as exploiting and manufacturing compatible cloning or restriction sites.

Typically, the nucleic acid sequence will be a gene which encodes the desired CREB protein, CREB analog, CREB-like molecule, CREB fusion protein or CREB function modulator. Such a gene is typically operably linked to suitable control sequences capable of effecting the expression of the CREB protein or CREB function modulator, preferably in the CNS. The term "operably linked", as used herein, is defined to mean that the gene (or the nucleic acid sequence) is linked to control sequences in a manner which allows expression of the gene (or the nucleic acid sequence). Generally, operably linked means contiguous.

Control sequences include a transcriptional promoter, an optional operator sequence to control transcription, a sequence encoding suitable messenger RNA (mRNA) ribosomal binding sites and sequences which control termination of transcription and translation. In a particular embodiment, a recombinant gene (or a nucleic acid sequence) encoding a CREB protein, CREB analog, CREB-like molecule, biologically active CREB fragment, CREB fusion protein or CREB function modulator can be placed under the regulatory control of a promoter which can be induced or repressed, thereby offering a greater degree of control with respect to the level of the product.

As used herein, the term "promoter" refers to a sequence of DNA, usually upstream (5') of the coding region of a structural gene, which controls the expression of the coding region by providing recognition and binding sites for RNA polymerase and other factors which may be required for initiation of transcription. Suitable promoters are well known in the art. Exemplary promoters include the SV40 and human elongation factor (EFI). Other suitable promoters are readily available in the art (see, e.g., Ausubel et al., Current Protocols in Molecular Biology, John Wiley & Sons, Inc., New York (1998); Sambrook et al., Molecular Cloning: A Laboratory Manual, 2nd edition, Cold Spring Harbor University Press, New York (1989); and U.S. Pat. No. 5,681,735).

Augmenting agents can enhance CREB pathway function by a variety of mechanisms. For example, an augmenting agent can affect a signal transduction pathway which leads to induction of CREB-dependent gene expression. Induction of CREB-dependent gene expression can be achieved, for example, via up-regulation of positive effectors of CREB function and/or down-regulation of negative effectors of CREB function. Positive effectors of CREB function include adenylate cyclases and CREB activators. Negative effectors of CREB function include cAMP phosphodiesterase (cAMP PDE) and CREB repressors.

An augmenting agent can enhance CREB pathway function by acting biochemically upstream of or directly acting on an activator or repressor form of a CREB protein and/or on a CREB protein containing transcription complex. For example, CREB pathway function can be affected by increasing CREB protein levels transcriptionally, post-transcriptionally, or both transcriptionally and post-transcriptionally; by altering the affinity of CREB protein to other necessary components of the of the transcription complex, such as, for example, to CREB-binding protein (CBP protein); by altering the affinity of a CREB protein containing transcription complex for DNA CREB responsive elements in the promoter region; or by inducing either passive or active immunity to CREB protein isoforms. The particular mechanism by which an augmenting agent enhances CREB pathway function is not critical to the practice of the invention.

Augmenting agents can be administered directly to an animal in a variety of ways. In a preferred embodiment, augmenting agents are administered systemically. Other routes of administration are generally known in the art and include intravenous including infusion and/or bolus injection, intracerebroventricularly, intrathecal, parenteral, mucosal, implant, intraperitoneal, oral, intradermal, transdermal (e.g., in slow release polymers), intramuscular, subcutaneous, topical, epidural, etc. routes. Other suitable routes of administration can also be used, for example, to achieve absorption through epithelial or mucocutaneous linings. Particular augmenting agents can also be administered by gene therapy, wherein a DNA molecule encoding a particular therapeutic protein or peptide is administered to the animal, e.g., via a vector, which causes the particular protein or peptide to be expressed and secreted at therapeutic levels in vivo.

A vector, as the term is used herein, refers to a nucleic acid vector, e.g., a DNA plasmid, virus or other suitable replicon (e.g., viral vector). Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, Spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

A nucleic acid sequence encoding a protein or peptide (e.g., CREB protein, CREB analog (including CREM, ATF-1), CREB-like molecule, biologically active CREB fragment, CREB fusion protein, CREB function modulator) can be inserted into a nucleic acid vector according to methods generally known in the art (see, e.g., Ausubel et al., Eds., Current Protocols in Molecular Biology, John Wiley & Sons, Inc., New York (1998); Sambrook et al., Eds., Molecular Cloning: A Laboratory Manual, 2nd edition, Cold Spring Harbor University Press, New York (1989)).

The mode of administration is preferably at the location of the target cells. In a particular embodiment, the mode of administration is to neurons.

Augmenting agents can be administered together with other components of biologically active agents, such as pharmaceutically acceptable surfactants (e.g., glycerides), excipients (e.g., lactose), stabilizers, preservatives, humectants, emollients, antioxidants, carriers, diluents and vehicles. If desired, certain sweetening, flavoring and/or coloring agents can also be added.

Augmenting agents can be formulated as a solution, suspension, emulsion or lyophilized powder in association with a pharmaceutically acceptable parenteral vehicle. Examples of such vehicles are water, saline, Ringer's solution, isotonic sodium chloride solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation can be sterilized by commonly used techniques. Suitable pharmaceutical carriers are described in Remington's Pharmaceutical Sciences.

The dosage of augmenting agent administered to an animal is that amount required to effect a change in CREB-dependent gene expression, particularly in neurons. The dosage administered to an animal, including frequency of administration, will vary depending upon a variety of factors, including pharmacodynamic characteristics of the particular augmenting agent, mode and route of administration; size, age, sex, health, body weight and diet of the recipient; nature and extent of symptoms being treated or nature and extent of the cognitive function(s) being enhanced or modulated, kind of concurrent treatment, frequency of treatment, and the effect desired.

Augmenting agents can be administered in single or divided doses (e.g., a series of doses separated by intervals of days, weeks or months), or in a sustained release form, depending upon factors such as nature and extent of symptoms, kind of concurrent treatment and the effect desired. Other therapeutic regimens or agents can be used in conjunction with the present invention.

The present invention will now be illustrated by the following example, which is not to be considered limiting in any way.

EXAMPLE

Subjects were 103 adult male Sprague-Dawley rats (Taconic, Gremantown, N.Y.) weighing between 275-300 g at the onset of experimentation. Rats were single housed in a temperature-controlled animal facility with a 12:12 h light-dark cycle and had access to food and water ad libitum. All animal protocols conformed to NIH guidelines and were approved by Cold Spring Harbor Laboratory Animal Care and Use Committee.

Motor Rehabilitation with the Staggered Step Task

The staggered step task used in this study was characterized previously by Klint et al., Journal of Neurotrauma, 21st Annual National Neurotrauma Society Symposium, 20(10): (2003). It consists of a runway 8' long and 3.5' wide upon which a series of 28 raised steps are attached. Steps were alternately "staggered"0.5 cm from midline and 25 cm between steps. This positioning placed the top walking surface directly in line with the natural walking gait of a 350 g rat. A thin piece of Plexiglas (8' long 2.5" wide 2 mm thick) was placed the center of the runway to prevent rats from weaving in-between the steps and also to serve as a crutch for animals to regain footing after falling off the walking surface of the steps. The sides and top of the runway were enclosed in Plexiglas to limit the animal's lateral and vertical movement. Darkened home boxes (12"×12"×12") were attached to both ends of the runway. A bright light and speaker with white noise generator were attached to the interior of the home box and exterior side of the home box such that it was enclosed within the runway. A computer controlled door was used to manage entrance/exit from the home boxes.

On days 1-13 rats were handled, habituated to the runway, and trained to freely traverse the runway by stepping on the top surface of the steps. Once acclimated to the runway, rats were trained using a negative reinforcement training paradigm to (1) exit a home box, (2) traverse the runway and (3) enter the opposite home box to terminate a negative stimulus (bright light and white noise). After 60 sec rest interval the rat was then trained to return to the original home box using the same negative reinforcement training paradigm. Beginning on day 14 of training, rats were trained daily for 5 trials until they met a criteria performance (latency <12 sec, and 1 or fewer total errors on 3 consecutive crossings). An error was scored every time a paw slipped off a step or a directed step was taken that did not land on the top surface of the step.

Twenty four hours after a rat reached criteria, it was injured using the LFP device. The animal was allowed to recover for 7 days. On day 8 post-injury, the rat was tested for baseline performance (3 crossings) on the staggered step task. The following day the animal was randomly assigned to one of 5 treatment groups: vehicle with rehabilitation (n=11), 0.15 mg/kg of HT-0712 with rehabilitation (n=13), 0.1 mg/kg of rolipram with rehabilitation (n=11), 0.15 mg/kg HT-0712 with no rehabilitation, (n=10) or vehicle with no rehabilitation (n=10). Injections were given i.p. 20 min prior to rehabilitation, (or once daily for the no rehabilitation groups). Rehabilitation/injections were repeated for 8 consecutive days. On day 10, (the last day of rehabilitation) no injections were given and all rats were tested again for performance on the SS task.

Trace Conditioning

One week after completing motor rehabilitation, rats were trained for trace fear conditioning. A standardized rat contextual fear conditioning apparatus (Med Associates, Inc., VA) was placed within a darkened sound-attenuating box (Med Associates, Inc., VA). On the training day, the rat was placed into the conditioning chamber for 2 minutes before the onset of the conditioned stimulus (CS), a 2800 Hz tone, which lasted for 20 seconds at 75 dB. Thirty seconds after the end of the tone, a 0.5 mA shock unconditioned stimulus (US) was delivered to the animal for two seconds. A 3 minute inter-trial interval separated the offset of the US and the proceeding CS. Rats were trained for 5 pairings of CS and US. After the last US, the rat was left in the chamber for an additional 30 seconds and then returned to its home cage. After each experimental subject, the apparatus was thoroughly cleaned with 75% ethanol, water, dried, and ventilated. Rats were tested 7 days after training. To differentiate the context from the training day, testing was performed in a novel sound attenuation chamber and internal chambers with novel dimensions, colors, textures and lighting. The chamber was cleaned using a Windex solution instead of ethanol. Each test began with 120 seconds of habituation, then 20 seconds of tone (CS), followed by an additional 240 second rest interval, until the CS was presented 3 times. Freezing was scored in five-second intervals. Freezing was defined as the complete lack of movement for 3 of 5 seconds. A percent freezing score was calculated by subtracting the percent of pre-CS freezing (during the initial 120 seconds) from the total percent freezing following the CS. Each experiment was filmed. In all experiments, the experimenter was blind to the drug treatment and training conditions of subjects.

Cognitive Rehabilitation with Repeated Novel Object Recognition

The open exploration arena (a black Plexiglas box 80 cm long, 60 cm wide, and 50 cm tall, illuminated indirectly to 55 lumens) contained a thin layer of cage bedding, which was replaced with half fresh bedding at the beginning of each day. A video camera mounted directly above the arena recorded all training and testing sessions. Objects were placed onto marked positions in the central area of the box, and the spatial position of the objects (left-right sides) was counterbalanced between subjects. Prior to OR training, animals were handled and habituated to the exploration arena for 4 min per day for 3 consecutive days. For training, rats freely explored the exploration arena containing two identical objects (e.g. candlesticks) for 7.5 minutes. Twenty-four hours after training, the rat was placed back into the exploration arena for 5 min with one object it had explored the previous day and one novel object of similar size. For the purpose of this study we will refer to a training session and the following testing session 24 hrs later a single "Trial." One day (24 hrs) after completion of a trial, animals started a new trial by training to a new set of identical objects, followed by a testing sessions the following day. During cognitive rehabilitation, rats were either trained or tested without any days of rest. In total each rat was trained to 17 pairs of objects (5 prior to injury and 13 post-injury). During training, the number of approaches and the time spent exploring each object was recorded. During testing, the time spent exploring each object was recorded. A discrimination index was calculated with exploration time of the novel and old objects, using the following formula ((novel object−old object)/(new object+old object))*100.

The time course of the cognitive rehabilitation was as follows. See FIG. 1 for graphical representation of rehabilitation procedure: Day 1-10: Trials 1-5, pre-injury analysis; Day 11: induction of experimental traumatic brain injury (TBI); Day 12-18: recovery from TBI; Day 19-20: Trial 6, post-injury baseline (BS1); Day 21-22: Trial 7, training with drug (TD1); Day 23: Trial 8, short term memory (STM) test 4 hr interval between training and testing with no drug; Day 24-25: Trial 9, establish second baseline (BS2) performance prior to drug assisted rehabilitation; Day 26-34: Trials 10-14, drug assisted cognitive rehabilitation (drug given 20 prior to training); Day 35-36: Trial 15, first post-rehab memory assessment (Ass1) no drug at time of training; Day 42-43: Trial 16, second post-rehab memory assessment (Ass2) after 1 week of rest; Day 79-79: Trial 17, third post-rehab memory assessment (Ass3) after 5 weeks of rest; Day 85: trace conditioning; Day 92: trace conditioning test.

Induction of Traumatic Brain Injury

Traumatic brain injury was produced using the well characterized lateral fluid percussion model (LFP) (Mcintosh et al., Neuroscience, 28(1):233-44 (1989), Hallam et al., J Neurotrauma, 21(5):521-39 (2004). Briefly, rats were anesthetized, intubated, and mechanically ventilated with 2% isoflurane using surgical air as a carrier gas. Body temperature was monitored and maintained at 37.5±0.5° C. by a feedback temperature controller (Physitemp Instruments, Clifton, N.J.). A midline incision was made in the scalp and a 4.8 mm circular craniotomy was performed midway between lambda and bregma, 3.0 mm to the right of the central suture. A modified leur-lock connector (trauma cannula), 2.6 mm inner diameter, was secured into the craniotomy with cyanoacrylic adhesive and dental acrylic. TBI was produced by rapidly injecting a small volume of saline into the closed cranial cavity with a fluid percussion device (VCU Biomedical Engineering, Richmond, Va.). The animal was then removed from the device, the acrylic and cannula removed, and the incision sutured. Ventilation was continued with room air without isoflurane until spontaneous breathing resumed. The LFP device was calibrated to a severe (3.2 atm) brain injury. This brain injury resulted in a 34% mortality rate (22 of 30 rats were survived for OR study, and 57 of 85 rats survived in the SS study).

Drug Preparation and Injection

The PDE4 inhibitors HT-0712 (0.15 mg/kg) or Rolipram (0.1 mg/kg) were delivered in a saline vehicle containing 1.5% dimethyl sulfoxide (DMSO) and 10% Cremophor. This dose was chosen from previous studies showing 0.15 mg/kg of HT-0712 was the most efficacious dose for enhancing motor memory in rats (McDonald et al., Society for Neuroscience, Vol. 24, Abstract 681.7. (2004)

Statistical Analysis

All data are expressed as means±SEM. Data analysis was performed using SPSS 12.0 software (SPSS, Chicago, Ill.). Significance level was P<0.05 for all tests. For comparison of pre-injury to post-injury performance on the staggered step, a paired t test was performed using all groups for analysis. An ANOVA was performed between groups for analyzing post-injury baselines (day 1) and post-rehab locomotor assessment (day 10). For analysis of staggered step rehabilitation (days 2-10), the dependant variable (foot faults or latency) was analyzed using repeated-measures ANOVA with days as the repeated within subjects variable. Dunnett's post-hoc tests were performed to determine statistical differences between vehicle injected and drug injected groups. For analysis of object recognition and trace conditioning data, Student's unpaired t tests were used to compare between groups on each testing day.

Results

PDE4 Inhibitors Enhance Motor Rehabilitation

Our previous experiments on normal, young-adult mice established that long-term memory formation was enhanced by the PDE4 inhibitors HT-0712 and rolipram (Bourtchouladze R., et al. (2003) A mouse model of Rubinstein Taybi Syndrome: defective long-term memory is ameliorated by inhibitors of phosphodiesterase 4. *Proceedings of the National Academy of Science U.S.A.* 100: 10518-10522; Scott R., et al., (2002) CREB and the discovery of cognitive enhancers. *Journal of Molecular Neuroscience* 19: 171-177; Tully T., et al. (2003) Targeting the CREB pathway for memory enhancers. *Nature Reviews Drug Discovery* 2:267-77). Specifically, these drugs enhance memory formation by reducing the amount of training required to produce maximal long-term memory. Whether these PDE4 inhibitors could facilitate motor rehabilitation following brain injury in rats was tested by reducing the amount of rehabilitation needed to recover skilled locomotor function. To that end, rats were trained to a criterion performance on a skilled locomotor task, the staggered step task. After reaching criteria performance, rats were injured using the LFP brain injury device and allowed to recover for 1 week. Seven days after injury (rehab day 1), all brain injured groups had a significant disruption in gait and skilled locomotor stepping accuracy as measured by a significant increase in foot faults ($t=-18.36$, $p=4.28e^{-25}$) (FIG. 2A) and crossing latency ($t=-13.52$, $p=7.86e^{-19}$) (FIG. 2B) compared to pre-injury baseline. An ANOVA on rehab day 1 revealed no significant differences in post-injury baseline performance between treatment groups ($F_{4,50}=0.646$, $p=0.632$). The following day, rats were randomly assigned to receive either daily administration of vehicle/PDE4 inhibitors with rehabilitation or daily injection of vehicle/PDE4 inhibitors without rehabilitation. For rats receiving rehabilitation, a significant effect of drug treatment on staggered step errors ($F_{2,32}=7.50$, $p=0.02$) and latency was observed. Dunnett post-hoc analysis revealed that both the HT-0712 group ($p=0.008$) and the rolipram group ($p=0.004$) performed significantly better than the vehicle treated group.

In addition, whether daily injection of vehicle/HT-0712 without daily rehabilitation would improve performance on the final testing day was assessed. An ANOVA comparison on day 10 showed a significant effect of treatment ($F_{4, 50}=10.11$, $p=0.00004$). Post-hoc Bonferroni analysis revealed no significant differences between vehicle groups ($p=1.0$), and no significant differences between PDE4 inhibitor groups ($p=1.0$). However, all groups receiving daily injections of PDE4 inhibitors performed significantly better than all vehicle injected controls (not all comparisons shown). Specifically the HT-0712 group with no rehabilitation performed significantly better than the vehicle group with no rehabilitation ($p=0.01$) and significantly better than the vehicle group with rehabilitation ($p=0.028$).

PDE4 Inhibitors Enhance Cognitive Rehabilitation

Our previous experiments have shown that the PDE4 inhibitors rolipram and HT-0712 can ameliorate long term memory deficits in mice, specifically, CBP$^{+/-}$ mutant mice. These CBP$^{+/-}$ mutant mice are a mouse model of Rubenstein-Taybi syndrome and have memory deficits caused by a molecular lesion in the CREB pathway (Bourtchouladze et al., Proc Natl Acad Sci USA., 100(18):10518-22, (2003); Olike et al., Hum Mol Genet. 8(3):387-96. (1999)). Treatment with the PDE4 inhibitor HT-0712 at the time of training was able to restore long-term memory function to levels similar to wild type mice. Numerous studies have shown that LFP injured rats have deficits in long term memory (cite). Two main hypotheses were tested, (1) could a single administration of the PDE4 inhibitor HT-0712 given at the time of training ameliorate the memory deficits in observed brain injured rats, and (2) could the PDE4 inhibitor HT-0712 be used to facilitate cognitive rehabilitation in brain injured rats. To test these hypotheses, a task was needed that: 1) required long term memory formation, 2) allowed for repeated training and testing of memory performance, and 3) ensured performance on an individual trial was not confounded by memory performance on a previous trial. The object recognition task met all three of these requirements. Object recognition is a non-aversive task that relies on a rat's natural exploratory behavior. During training for this task, rats are presented with two identical objects. Given adequate exposure (training time), normal rats form a LTM of an explored object. When rats are presented with two different objects (i.e. one novel object and one previously explored object) rats will choose to spend more time exploring a novel object (cite). This task can be performed repeatedly on the same animals by exposing them serially to different sets of novel objects. Thus, object recognition is an ideal task to test these hypotheses.

Prior to injury, rats were trained/tested for 5 trials for object recognition memory 24 hrs after training. On all trials, rats retained a memory of the previously explored object and displayed a preference for the novel object (FIG. 3E). There were no significant differences in memory performance between groups which would later receive drug or vehicle (FIG. 3E). Therefore, all pre-injury discrimination indices for each group were averaged and a pre-injury baseline performance for each group was obtained (FIG. 3A). Again there were no significant differences between groups ($p=0.391$). Upon completion of trial 5, rats were injured with the LFP device and allowed to recover for 7 days. On the first baseline trial following injury (FIG. 3B), both groups displayed long term memory deficits for object recognition. There was no statistically significant difference between groups ($p=0.665$) on this first baseline assessment. Thus, experimental brain injury resulted in memory deficits in object recognition.

Next, whether the PDE4 inhibitor HT-0712 could enhance long term memory for object recognition in brain injured rats was determined. Rats were randomly assigned to a treatment group and injected 20 minutes prior to the training session with either vehicle or HT-0712. After testing, the group receiving HT-0712 showed a preference for the novel object and performed significantly better than the vehicle group ($p=0.001$) (FIG. 3B). Hence, a single administration of the PDE4 inhibitor HT-0712 could ameliorate the long-term memory deficit observed in brain injured rats.

Next, whether these rats had dysfunctional short term memory in addition to long term memory deficits was determined. To test this, both groups (without drug) were trained and tested for short term (4 hr) memory retention. Both groups showed retention of the previously explored object and had a preference for the novel object 4 hr after training (FIG. 3C). There were no significant differences between groups ($p=0.311$). Therefore, LFP injury disrupted the rats' long term memory for object recognition, but left short term memory unaffected to the point where the rats could perform normally at 4 hrs after training.

In order to determine if the single administration of HT-0712 changed the rat's long term memory performance, animals were trained for a second time without drug or vehicle injection (FIG. 4A, day 0). Upon testing there was no significant difference between vehicle and HT-0712 groups ($p=0.607$). This indicated that although a single injection of HT-0712 could enhance long term memory for that trial, a single drug administration did not ameliorate the animals object recognition memory deficits.

Drug assisted cognitive rehabilitation with HT-0712 was started. Rats were given 5 trials of OR training/testing. Rats were administered either vehicle or HT-0712 at 20 min prior to each training session. On rehab day 1 ($p=0.001$), day 2 ($p=0.001$), day 3 ($p=0.007$), and day 5 ($p=0.001$), the HT-0712 group performed significantly better than the vehicle group.

To assess any improvement in long term memory function following drug assisted cognitive rehabilitation, rats were trained/tested without drug treatment. The group which received HT-0712 assisted cognitive rehabilitation performed significantly better that the vehicle group ($p=0.003$) (FIG. 4B). This implies that the PDE4 inhibitor HT-0712 given during repeated cognitive rehabilitation was able to ameliorate the long term memory deficits for object recognition observed in brain injured rats.

Whether the observed amelioration of long term memory deficits was due to a sub-acute effect of repeated HT-0712 administration, or a true rehab effect was determined. Therefore, the rats were allowed to rest for 1 week and assessed long term memory function without drug. Again the effect of PDE4 assisted cognitive rehabilitation persisted, and the HT-0712 group performed better than the vehicle treated group ($p=0.04$) (FIG. 4C).

In order to determine if this effect was long lasting, the rats were allowed to rest for 7 weeks. After which they were handled and re-habituated them to the OR arena. Following re-habituation (8 weeks after the end of rehab), the rats were tested for OR performance. Again the group receiving HT-0712 assisted rehabilitation performed significantly better than the vehicle treated group ($p=0.012$) (FIG. 5A). From this 2 conclusions can be drawn, first that LFP brain injury results in long lasting deficits in long term memory for an object recognition task, and, second, HT-0712 assisted cognitive rehabilitation can ameliorate these long term memory deficits for an object recognition task.

In order to determine if this rehabilitation was specific to object recognition or if it generalized to other hippocampal dependent tasks, the rats were tested for memory performance on trace fear conditioning task. In this hippocampal dependent version of this task rats are trained to associate a tone (CS) with a shock (US). A 30 sec "trace" interval separates the CS and US, making this a hippocampal dependant task (McEcheron et al., Hippocampus, 8(6):638-46, (1998). When the rats were tested 1 week after training, the group receiving HT-0712 assisted cognitive rehabilitation performed significantly better than the vehicle group ($p=0.012$) (FIG. 5B). This implies that the HT-0712 assisted cognitive rehabilitation generalized to a second hippocampal dependant task.

Because the cognitive rehabilitation generalized from one hippocampal dependant task to another, whether PDE4 assisted rehabilitation was specific to the method of rehab or does it generalize improvements in multiple modalities was determined. Specifically, would the animals which also received PDE4 assisted motor rehabilitation also gain improved memory performance on a non-motor task? To that end, 1 week following PDE4 assisted motor rehabilitation, the motor rehab rats were trained on the trace fear conditioning task and tested them 1 week later. There were no significant differences between any of the motor rehabilitation groups (p=0.185) (FIG. 5C)

A direct statistical comparison between the motor rehab animals and the cognitive rehab animals for trace fear memory is questionable. A much greater pre-CS freezing (data not shown) was observed in the motor-rehabilitation groups. It is possible that as a result of the negative reinforcement training paradigm used to motivate animals on the staggered step task, the animals had a generalized heightened fear to any non-homecage environment. This increased generalized fear displayed as freezing may have masked any effect of treatment All publications, patent and patent applications mentioned in this specification are incorporated herein by reference to the same extent as if each individual publication, patent or patent application was specifically and individually incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method comprising:
    (a) providing cognitive training to an animal having a central nervous system disorder or condition under conditions sufficient to produce an improvement in performance by said animal of a cognitive task whose deficit is associated with said central nervous system (CNS) disorder or condition, wherein said deficit is a memory deficit;
    (b) administering in conjunction with said cognitive training a phosphodiesterase inhibitor that enhances CREB pathway function during said cognitive training;
    (c) repeating said providing and administering of steps (a) and (b) one or more times; and
    (d) reducing the number of training sessions sufficient to produce said improvement in performance relative to the improvement in performance produced by cognitive training alone;
    wherein said CNS disorder or condition is a neurodegenerative disease or condition; and
    wherein said phosphodiesterase inhibitor is HT-0712:

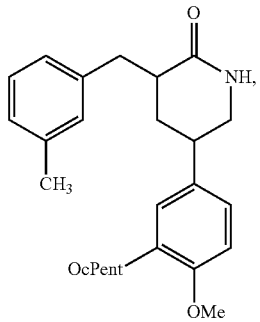

wherein "Me" means "methyl" and "cPent" means "cyclopentyl" or an enantiomer or a mixture thereof.

2. The method of claim 1, wherein said animal is a human.

3. A method comprising:
    (a) training an animal under conditions sufficient to stimulate neuronal activity or a pattern of neuronal activity underlying one or more neuronal circuits in an animal;
    (b) administering in conjunction with said training a phosphodiesterase inhibitor that enhances CREB pathway function during said training;
    (c) repeating said training and administering of steps (a) and (b) one or more times; and
    (d) reducing the number of training sessions sufficient to provide an improvement in function in said one or more neuronal circuits in said animal relative to the improvement in function produced by training alone;
    wherein said animal has a memory deficit associated with a neurodegenerative disease or condition; and
    wherein said phosphodiesterase inhibitor is HT-0712:

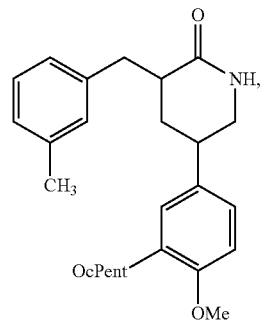

wherein "Me" means "methyl" and "cPent" means "cyclopentyl" or an enantiomer or a mixture thereof.

4. The method of claim 3, wherein said animal is a human.

5. The method of claim 1, wherein said cognitive training comprises spaced training sessions.

6. The method of claim 3, wherein said training comprises spaced training sessions.

7. The method of claim 5, wherein said phosphodiesterase inhibitor is administered before one or more training sessions.

8. The method of claim 6, wherein said phosphodiesterase inhibitor is administered before one or more training sessions.

* * * * *